(12) United States Patent
Zhu et al.

(10) Patent No.: US 7,550,603 B2
(45) Date of Patent: Jun. 23, 2009

(54) 1H-BENZIMIDAZOLE-4-CARBOXAMIDES SUBSTITUTED WITH A QUATERNARY CARBON AT THE 2-POSITION ARE POTENT PARP INHIBITORS

(75) Inventors: Gui-Dong Zhu, Gurnee, IL (US); Jianchun Gong, Deerfield, IL (US); Virajkumar B. Gandhi, Park City, IL (US); Thomas D. Penning, Elmhurst, IL (US); Vincent L. Giranda, Gurnee, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 0 days.

(21) Appl. No.: 11/401,638

(22) Filed: Apr. 11, 2006

(65) Prior Publication Data

US 2006/0229289 A1 Oct. 12, 2006

Related U.S. Application Data

(60) Provisional application No. 60/670,204, filed on Apr. 11, 2005.

(51) Int. Cl.
*A61K 31/4184* (2006.01)
*C07D 403/04* (2006.01)

(52) U.S. Cl. .................. 548/304.7; 548/306.1
(58) Field of Classification Search .............. 548/304.7, 548/306.1
See application file for complete search history.

(56) References Cited

U.S. PATENT DOCUMENTS

| 3,864,385 | A | 2/1975 | Feit et al. |
|---|---|---|---|
| 4,093,726 | A | 6/1978 | Winn et al. |
| 6,372,736 | B1 | 4/2002 | Kemp et al. |
| 6,448,271 | B1 * | 9/2002 | Lubisch et al. ............ 514/322 |
| 6,509,365 | B1 | 1/2003 | Lubisch et al. |
| 6,696,437 | B1 | 2/2004 | Lubisch et al. |
| 6,737,421 | B1 | 5/2004 | Lubish et al. |
| 7,166,292 | B2 | 1/2007 | Isele et al. |
| RE39,608 | E | 5/2007 | Lubisch et al. |
| 2003/0100582 | A1 | 5/2003 | Sircar et al. |

FOREIGN PATENT DOCUMENTS

| DE | 3522230 | 6/1985 |
|---|---|---|
| DE | 3522230 | 1/1987 |
| DE | 38 30 060 | 3/1990 |
| DE | 3830060 | 3/1990 |
| DE | 19916460 | 6/2000 |
| DE | 199 16 460 | 10/2000 |
| DE | 100 21 468 | 8/2001 |
| DE | 10021468 | 11/2001 |
| GB | 1354554 | 8/1971 |
| WO | WO 97/04771 | 2/1997 |
| WO | WO 9839343 | 9/1998 |
| WO | 0026192 | 5/2000 |
| WO | 00/32579 | 8/2000 |
| WO | 00/26192 | 11/2000 |
| WO | 0121615 | 3/2001 |
| WO | WO 01/21615 | 3/2001 |
| WO | WO-01/21615 A1 * | 3/2001 |
| WO | WO 01/21634 | 3/2001 |
| WO | WO 01/82877 | 11/2001 |
| WO | WO 02/068407 | 9/2002 |
| WO | WO-02/068407 A1 * | 9/2002 |
| WO | 03/002698 | 1/2003 |
| WO | 03020698 | 3/2003 |
| WO | WO 03/094861 | 11/2003 |
| WO | WO 03/106430 | 12/2003 |
| WO | WO 2004/054515 | 7/2004 |
| WO | WO 2004/065370 | 8/2004 |
| WO | 2004098494 | 11/2004 |
| WO | WO 2004/096793 | 11/2004 |
| WO | WO 2004/098494 | 11/2004 |

OTHER PUBLICATIONS

Alexy, et al., "Inhibition of ADP-Evoked Platelet Aggregation by Selected Poly(ADP-Ribose) Polymerase Inhibitors", Journal Cardiovasc Pharmacol 43,(3), 423-431 (2004).
Gilchrist, et al., "Cyclisation of ortho-Substituted N-Arylbenzimidoyl Nitrenes. Part 2. Preferential Cyclisations at an ortho-Position Bearing a Methoxycarbonyl Group", 1979.
Griffin, et al., "Resistance modifying agents. 3. Novel benzimidazole and quinazolinone inhibitors of the DNA repair enzyme poly(ADP-ribose)polymerase", Pharmaceutical Sciences, 2(1), 43-47 (1996).
Ohkura, et al., "Mechanism of the Color Reaction between m-Dinitrobenzene and Alkali Cyanide. II. Color Reaction Products of 2,4-Dinitroaniline with Postassium Cyanide (Organic Analysis. LXXII[1])", Chem Pharm Bull, 18(11), 2164-2168 (1970).
White, et al., Potentiation of cytotoxic drug activity in human tumor cell lines, by amine-substituted 2-arylbenzimidazol-4-carboxamide PARP-1 inh, 2004.
Burkart, V., et al., "Mice lacking the poly (ADP-ribose) polymerase gene are resistant to pancreatic beta-cell destruction and diabetes development induced by streptozocin", *Nat. Med.*, 5(3):314-319 (1999).

(Continued)

*Primary Examiner*—Laura L. Stockton
(74) *Attorney, Agent, or Firm*—Gregory W. Steele

(57) ABSTRACT

Compounds of Formula (I)

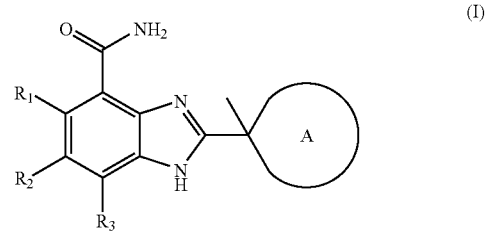

inhibit the PARP enzyme and are useful for treating a disease or a disorder associated with PARP. Also disclosed are pharmaceutical compositions comprising compounds of Formula (I), methods of treatment comprising compounds of Formula (I), and methods of inhibiting the PARP enzyme comprising compounds of Formula (I).

17 Claims, No Drawings

OTHER PUBLICATIONS

Chen, G. & Pan, Q.-c., "Potentiation of the antitumor activity of cisplatin in mice by 3-aminobenzamide and nicotinamide", *Cancer Chem. Pharm.*, 22:303-307 (1988).

Ehrlich, W., et al., "Inhibition of the induction of collagenase by interleukin-1β in cultured rabbit synovial fibroblasts after treatment with the poly(ADP-ribose)-polymerase inhibitor 3-aminobenzamide", *Rheumatol Int.*, 15:171-172 (1995).

Cuzzocrea, S., et al., "Protective effects of 3-aminobenzamide, an inhibitor of poly (ADP-ribose) synthase in a carrageenan-induced model of local inflammation", *Eur. J. of Pharm.*, 342:67-76 (1998).

IUPAC Comm. On Nomenclature of Organic Chemistry, "Rules for the Nomenclature of Organic Chemistry", *Section E: Stereochemistry*, 13-30 (1974).

Kröger, H., et al., "Synergistic Effects of Thalidomide and Poly(ADP-Ribose) Polymerase Inhibition of Type II Collagen-Induced Arthritis in Mice", *Inflammation*, 20(2):203-215 (1996).

Poste, G., et al., "Lipid Vesicles as Carriers for Introducing Biologically Active Materials into Cells", *Methods in Cell Biology*, XIV:33-71 (1976).

Szabo, C., et al., "Protection against peroxynitrite-induced fibroblast injury and arthritis development by inhibition of poly(ADP-ribose) synthase", *Proc. Natl. Acad. Sci. USA*, 95:3867-3872 (1998).

Thiemermann, C., et al., "Inhibition of the activity of poly (ADP ribose) synthhetase reduces ischemia-reperfusion injury in the heart and skeletal muscle", *Proc. Natl. Acad. Sci. USA*, 94:679-683 (1997).

Weltin, D., et al., "Immunosuppressive Activities of 6(5H)-Phenanthridinone, A New Poly(ADP-Ribose)Polymerase Inhibitor", *Int. J. Immunopharmac.*, 17(4):265-271 (1995).

Co-Pending U.S. Appl. No. 09/830,992, filed May 3, 2001.
Co-Pending U.S. Appl. No. 10/935,683, filed Sep. 7, 2004.
Co-Pending U.S. Appl. No. 11/401,635, filed Apr. 11, 2006.
Co-Pending U.S. Appl. No. 11/536,994, filed Sep. 29, 2006.
Co-Pending U.S. Appl. No. 11/560,166, filed Nov. 15, 2006.
Co-Pending U.S. Appl. No. 11/743,200, filed May 2, 2007.
Search Report No. 20030374, Jun. 13, 2003.
Search Report No. 20030487, Sep. 19, 2003.
Search Report No. 20050150, Apr. 22, 2005.
Search Report No. 20050207, May 27, 2005.

* cited by examiner

1H-BENZIMIDAZOLE-4-CARBOXAMIDES SUBSTITUTED WITH A QUATERNARY CARBON AT THE 2-POSITION ARE POTENT PARP INHIBITORS

This application claims priority from U.S. Provisional Patent Application Ser. No. 60/670,204, filed Apr. 11, 2005, incorporated herein by reference.

TECHNICAL FIELD

The present invention relates to 1H-benzimidazole-4-carboxamides substituted at the 2-position with a quaternary carbon, their preparation, and their use as inhibitors of the enzyme poly(ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing apoptosis of cancer cells, limiting tumor growth, decreasing metastasis, and prolonging the survival of tumor-bearing animals.

The present invention describes the finding that 1H-benzimidazole-4-carboxamides substituted with a quaternary carbon at the 2-position increases affinity for the PARP enzyme. The present invention describes benzimidazole derivatives of Formula (I) which have increased affinity and constitute potent PARP inhibitors.

SUMMARY OF THE INVENTION

In one embodiment, the present invention provides compounds of Formula (I)

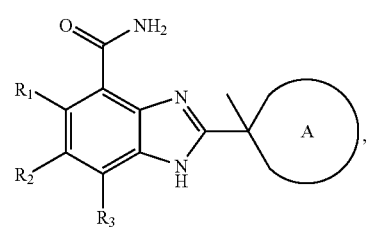

or a therapeutically acceptable salt thereof, wherein $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

A is a nonaromatic 4, 5, 6, 7, or 8-membered ring that contains 1 or 2 nitrogen atoms and, optionally, one sulfur or oxygen atom, wherein the nonaromatic ring is optionally substituted with 1, 2, or 3 substituents selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, nitro, oxo, $NR_CR_D$, $(NR_CR_D)$alkyl, $(NR_CR_D)$carbonyl, $(NR_CR_D)$carbonylalkyl, and $(NR_CR_D)$sulfonyl; and $R_A$, $R_B$, $R_C$, and $R_D$ are independently selected from the group consisting of hydrogen, alkyl, and alkycarbonyl.

DETAILED DESCRIPTION OF THE INVENTION

In another embodiment, the present invention provides compounds of Formula (I)

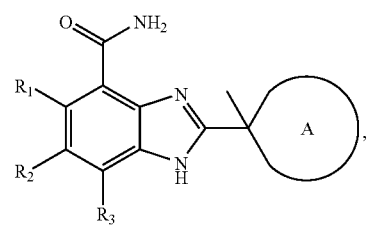

or a therapeutically acceptable salt thereof wherein $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl; A is selected from the group consisting of

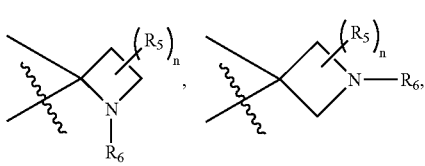

-continued

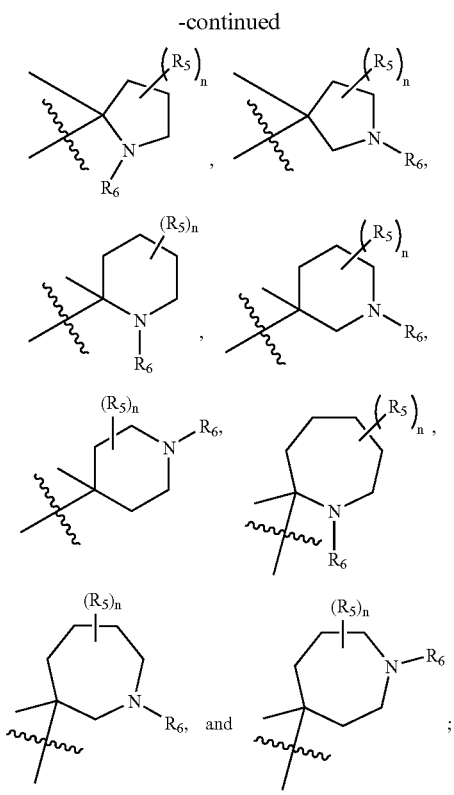

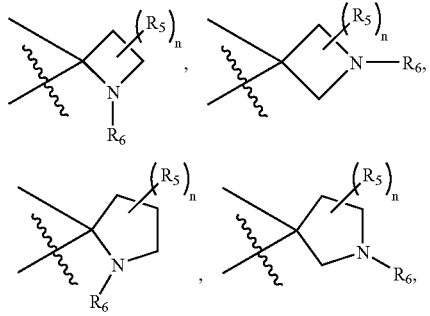

$R_5$ is independently selected from the group consisting of alkenyl, alkoxy, alkoxycarbonyl, alkyl, alkynyl, haloalkoxy, haloalkyl, halogen, hydroxy, hydroxyalkyl, $NR_CR_D$, and $(NR_CR_D)$carbonyl; n is 0, 1, 2, or 3; $R_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, oxo, $(NR_CR_D)$alkyl, $(NR_CR_D)$carbonyl, $(NR_CR_D)$carbonylalkyl, and $(NR_CR_D)$sulfonyl; $R_A$ and $R_B$ are independently selected from the group consisting of hydrogen, alkyl, and alkycarbonyl; and $R_C$ and $R_D$ are independently selected from the group consisting of hydrogen and alkyl.

In another embodiment, the present invention provides compounds of Formula (I) or a therapeutically acceptable salt thereof wherein $R_1$, $R_2$, and $R_3$ are hydrogen; A is selected from the group consisting of

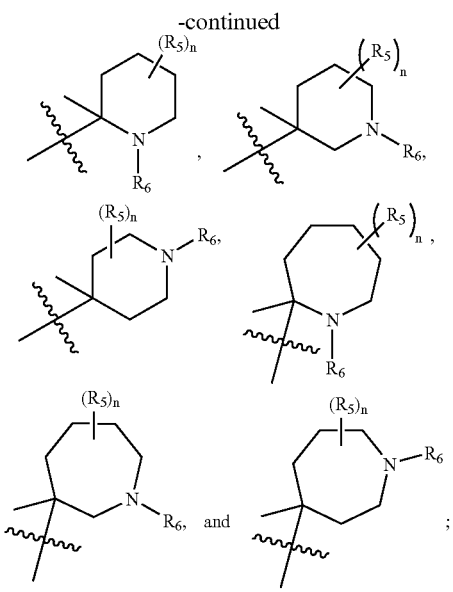

n is 0; $R_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, $(NR_CR_D)$alkyl, $(NR_CR_D)$carbonyl, $(NR_CR_D)$carbonylalkyl, and $(NR_CR_D)$sulfonyl; and $R_C$ and $R_D$ are independently selected from the group consisting of hydrogen and alkyl.

In another embodiment, the present invention provides compounds of Formula (I) wherein A is selected from the group consisting of

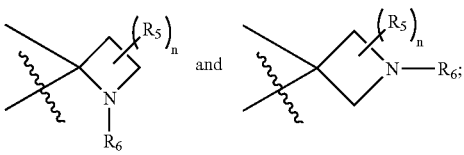

and n, $R_1$, $R_2$, $R_3$, $R_5$, and $R_6$ are as defined in Formula (I).

In another embodiment, the present invention provides compounds of Formula (I) wherein A is selected from the group consisting of

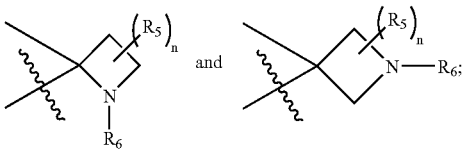

and n is 0; $R_1$, $R_2$, and $R_3$ are hydrogen; $R_6$ is selected from the group consisting of hydrogen, alkyl, $(NR_CR_D)$sulfonyl, and arylalkyl; and $R_C$ and $R_D$ are independently selected from the group consisting of hydrogen and alkyl.

In another embodiment, the present invention provides compounds of Formula (I) wherein A is selected from the group consisting of

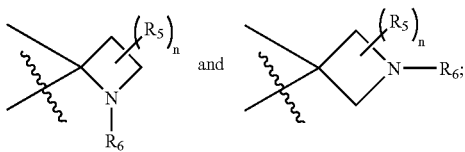

n is 0; $R_1$, $R_2$, and $R_3$ are hydrogen; and $R_6$ is selected from the group consisting of cycloalkyl and cycloalkylalkyl.

In another embodiment, the present invention provides compounds of Formula (I) wherein A is selected from the group consisting of

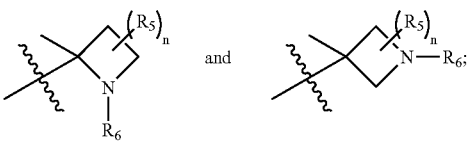

n is 0; $R_1$, $R_2$, and $R_3$ are hydrogen; and $R_6$ is heterocycle.

In another embodiment, the present invention provides compounds of Formula (I) wherein A is selected from the group consisting of

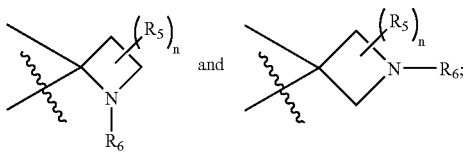

n is 0; $R_1$, $R_2$, and $R_3$ are hydrogen; and $R_6$ is heteroarylalkyl.

In another embodiment, the present invention provides compounds of Formula (I) wherein A is selected from the group consisting of

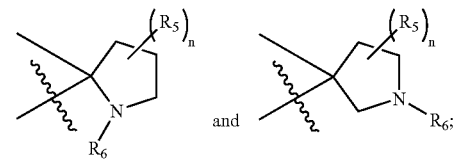

and n, $R_1$, $R_2$, $R_3$, $R_5$, and $R_6$ are as defined in Formula (I).

In another embodiment, the present invention provides compounds of Formula (I) wherein A is selected from the group consisting of

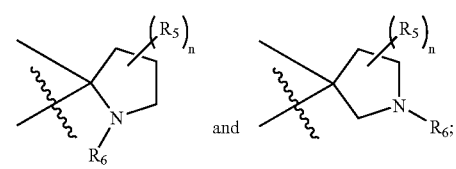

n is 0; $R_1$, $R_2$, and $R_3$ are hydrogen; $R_6$ is selected from the group consisting of hydrogen, alkyl, (NR$_C$R$_D$)sulfonyl, and arylalkyl; and R$_C$ and R$_D$ are independently selected from the group consisting of hydrogen and alkyl.

In another embodiment, the present invention provides compounds of Formula (I) wherein A is selected from the group consisting of

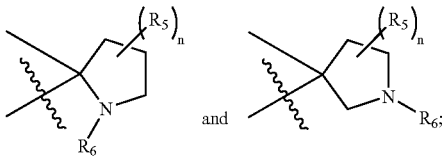

n is 0; $R_1$, $R_2$, and $R_3$ are hydrogen; and $R_6$ is selected from the group consisting of cycloalkyl and cycloalkylalkyl.

In another embodiment, the present invention provides compounds of Formula (I) wherein A is selected from the group consisting of

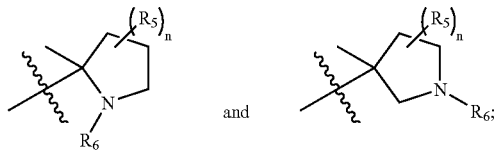

n is 0; $R_1$, $R_2$, and $R_3$ are hydrogen; and $R_6$ is heterocycle.

In another embodiment, the present invention provides compounds of Formula (I) wherein A is selected from the group consisting of

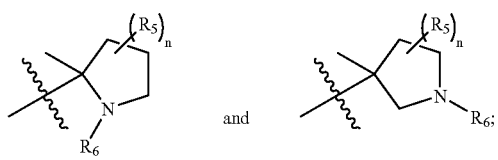

n is 0; $R_1$, $R_2$, and $R_3$ are hydrogen; and $R_6$ is heteroarylalkyl.

In another embodiment, the present invention provides compounds of Formula (I) wherein A is selected from the group consisting of

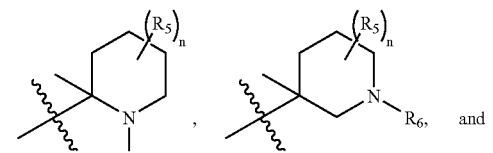 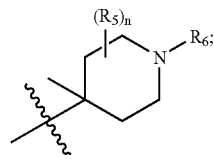

and n, $R_1$, $R_2$, $R_3$, $R_5$, and $R_6$ are as defined in Formula (I).

In another embodiment, the present invention provides compounds of Formula (I) wherein A is selected from the group consisting of

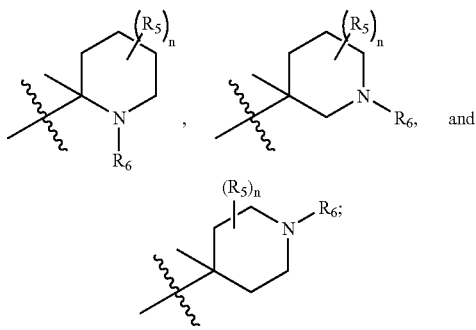

n is 0; $R_1$, $R_2$, and $R_3$ are hydrogen; $R_6$ is selected from the group consisting of hydrogen, alkyl, $(NR_CR_D)$sulfonyl, and arylalkyl; and $R_C$ and $R_D$ are independently selected from the group consisting of hydrogen and alkyl.

In another embodiment, the present invention provides compounds of Formula (I) wherein A is selected from the group consisting of

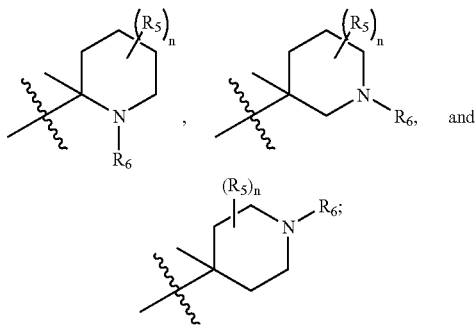

n is 0; $R_1$, $R_2$, and $R_3$ are hydrogen; and $R_6$ is selected from the group consisting of cycloalkyl and cycloalkylalkyl.

In another embodiment, the present invention provides compounds of Formula (I) wherein A is selected from the group consisting of

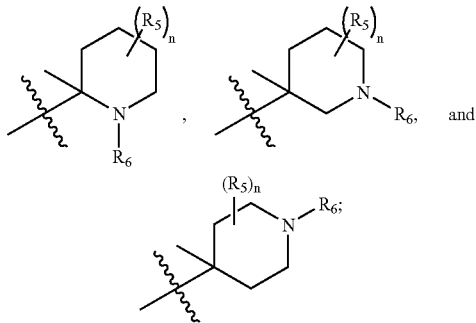

n is 0; $R_1$, $R_2$, and $R_3$ are hydrogen; and $R_6$ is heterocycle.

In another embodiment, the present invention provides compounds of Formula (II) wherein A is selected from the group consisting of

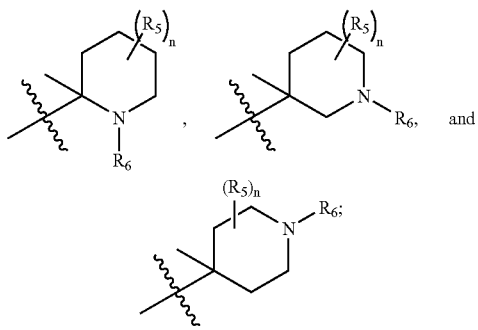

n is 0, $R_1$, $R_2$, and $R_3$ are hydrogen; and $R_6$ is heteroarylalkyl.

In another embodiment, the present invention provides compounds of Formula (I) wherein A is selected from the group consisting of

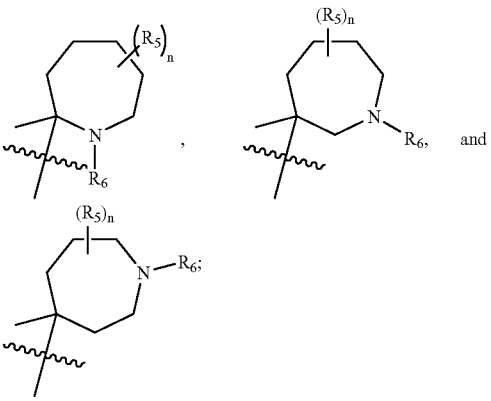

and n, $R_1$, $R_2$, $R_3$, $R_5$, and $R_6$ are as defined in Formula (I).

In another embodiment, the present invention provides compounds of Formula (I) wherein A is selected from the group consisting of

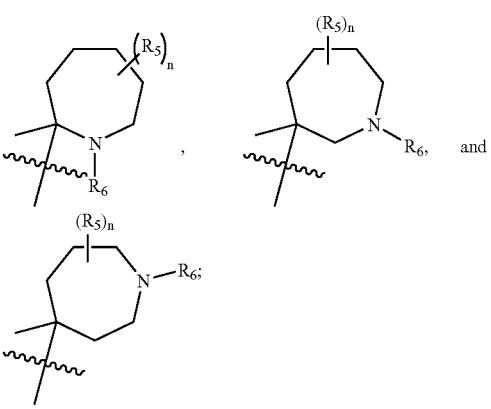

n is 0; $R_1$, $R_2$, and $R_3$ are hydrogen; $R_6$ is selected from the group consisting of hydrogen, alkyl, $(NR_CR_D)$sulfonyl, and arylalkyl; and $R_C$ and $R_D$ are independently selected from the group consisting of hydrogen and alkyl.

In another embodiment, the present invention provides compounds of Formula (I) wherein A is selected from the group consisting of

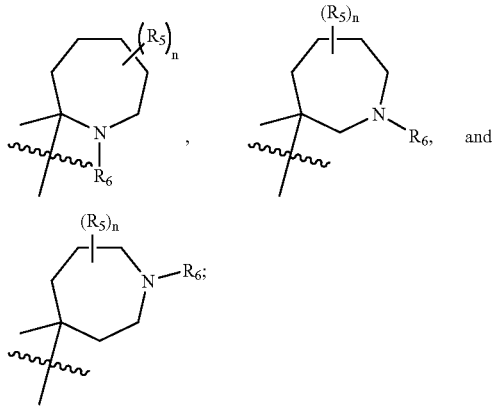

n is 0; $R_1$, $R_2$, and $R_3$ are hydrogen; and $R_6$ is selected from the group consisting of cycloalkyl and cycloalkylalkyl.

In another embodiment, the present invention provides compounds of Formula (I) wherein A is selected from the group consisting of

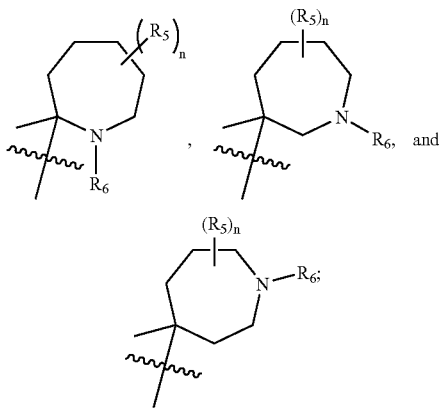

n is 0; $R_1$, $R_2$, and $R_3$ are hydrogen; and $R_6$ is heterocycle.

In another embodiment, the present invention provides compounds of Formula (I) wherein A is selected from the group consisting of

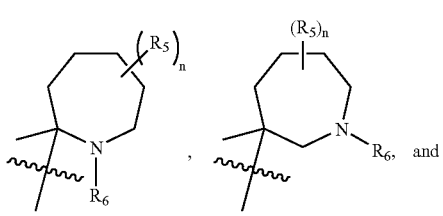

-continued

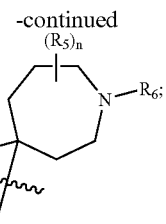

n is 0; $R_1$, $R_2$, and $R_3$ are hydrogen; and $R_6$ is heteroarylalkyl.

In another embodiment, the present invention provides a pharmaceutical composition comprising a compound of Formula (I), or a therapeutically acceptable salt thereof, in combination with a therapeutically acceptable carrier.

In another embodiment, the present invention provides a method of inhibiting PARP in a mammal in recognized need of such treatment comprising administering to the mammal a therapeutically acceptable amount of a compound of Formula (I) or a therapeutically acceptable salt thereof.

In another embodiment, the present invention provides a method of treating cancer in a mammal in recognized need of such treatment comprising administering to the mammal a therapeutically acceptable amount of a compound of Formula (I) or a therapeutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a therapeutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a method of treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a method of treating hypoglycemia in a mammal in recognized need of such treatment comprising administering to the mammal a therapeutically acceptable amount of a compound of Formula (I) or a therapeutically acceptable salt thereof.

In another embodiment, the present invention provides a method of treating retroviral infection in a mammal in recognized need of such treatment comprising administering to the mammal a therapeutically acceptable amount of a compound of Formula (I) or a therapeutically acceptable salt thereof.

In another embodiment, the present invention provides a method of treating liver toxicity following acetominophen overdose in a mammal in recognized need of such treatment comprising administering to the mammal a therapeutically acceptable amount of a compound of Formula (I) or a therapeutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for inhibiting the PARP enzyme in a mammal in recognized need of such treatment.

In another embodiment, the present invention provides a use of a compound of Formula (I), or a therapeutically acceptable salt thereof, to prepare a medicament for inhibiting tumor growth in a mammal in recognized need of such treatment.

In another embodiment, the present invention provides a use of a compound of Formula (I), or a therapeutically acceptable salt thereof, to prepare a medicament for treating cancer in a mammal in recognized need of such treatment.

In another embodiment, the present invention provides a use of a compound of Formula (I), or a therapeutically acceptable salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, the present invention provides a use of a compound of Formula (I), or a therapeutically acceptable salt thereof, to prepare a medicament for potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating hypoglycemia in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating retroviral infection in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating liver toxicity following acetominophen overdose in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating skin damage secondary to sulfur mustards in a mammal in recognized need of such treatment comprising administering to the mammal a therapeutically acceptable amount of a compound of Formula (I) or a therapeutically acceptable salt thereof.

DEFINITIONS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, appended to the parent molecular moiety through an alkyl group, as defined herein. Representative examples of alkoxyalkyl include, but are not limited to, tert-butoxyethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, $-NR_ER_F$, and $(NR_ER_F)$carbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "carbonyl" as used herein, means a $-C(O)-$ group.

The term "carboxy" as used herein, means a $-CO_2H$ group.

The term "cyano" as used herein, means a $-CN$ group.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycloalkyl groups of the present invention are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, oxo, $-NR_ER_F$, and $(NR_ER_F)$carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a $-C(O)H$ group.

The term "halo" or "halogen" as used herein, means $-Cl$, $-Br$, $-I$ or $-F$.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinymethyl.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocycles of this invention are substituted with 0, 1, 2, or 3 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "heterocyclealkyl" as used herein, means a heterocycle, as defined herein, appended to the parent molecular moiety through an alkyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "nonaromatic" as used herein, means that a 4 membered nonaromatic ring contains zero double bonds, a 5 membered nonaromatic ring contains zero or one double bond, a 6, 7, or 8 membered nonaromatic ring contains zero, one, or two double bonds.

The term "$NR_AR_B$" as used herein, means two groups, $R_A$ and $R_B$, which are appended to the parent molecular moiety through a nitrogen atom. $R_A$ and $R_B$ are each independently hydrogen, alkyl, and alkylcarbonyl. Representative examples of $NR_AR_B$ include, but are not limited to, amino, methylamino, acetylamino, and acetylmethylamino.

The term "($NR_AR_B$)carbonyl" as used herein, means a $NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, and (ethylmethylamino)carbonyl.

The term "$NR_CR_D$" as used herein, means two groups, $R_C$ and $R_D$, which are appended to the parent molecular moiety through a nitrogen atom. $R_C$ and $R_D$ are each independently hydrogen, alkyl, and alkylcarbonyl. Representative examples of $NR_CR_D$ include, but are not limited to, amino, methylamino, acetylamino, and acetylmethylamino.

The term "($NR_CR_D$)carbonyl" as used herein, means a $NR_CR_D$ group, as defined herein, appended to the parent molecular moiety through a carbonyl group, as defined herein. Representative examples of ($NR_CR_D$)carbonyl include, but are not limited to, aminocarbonyl, (methylamino)carbonyl, (dimethylamino)carbonyl, and (ethylmethylamino)carbonyl.

The term "($NR_CR_D$)carbonylalkyl" as used herein, means a ($NR_CR_D$)carbonyl group, as defined herein, appended to the parent molecular moiety through an alkyl group, as defined herein.

The term "($NR_CR_D$)sulfonyl" as used herein, means a $NR_CR_D$ group, as defined herein, appended to the parent molecular moiety through a sulfonyl group, as defined herein. Representative examples of ($NR_CR_D$)sulfonyl include, but are not limited to, aminosulfonyl, (methylamino)sulfonyl, (dimethylamino)sulfonyl, and (ethylmethylamino)sulfonyl.

The term "$NR_ER_F$" as used herein, means two groups, $R_E$ and $R_F$, which are appended to the parent molecular moiety through a nitrogen atom. $R_E$ and $R_F$ are each independently hydrogen, alkyl, and alkylcarbonyl. Representative examples of $NR_ER_F$ include, but are not limited to, amino, methylamino, acetylamino, and acetylmethylamino.

The term "($NR_ER_F$)carbonyl" as used herein, means a $NR_ER_F$ group, as defined herein, appended to the parent molecular moiety through a carbonyl group, as defined herein. Representative examples of ($NR_ER_F$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity

Inhibition of PARP

Nicotinamide[2,5',8-3H]adenine dinucleotide and strepavidin SPA beads were purchased from Amersham Biosiences (UK) Recombinant Human Poly(ADP-Ribose) Polymerase (PARP) purified from *E. coli* and 6-Biotin-17-$NAD^+$, were purchase from Trevigen, Gaithersburg, Md. $NAD^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissolved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM $MgCl_2$. PARP reactions contained 1.5 μM [$^3$H]-$NAD^+$ (1.6 uCi/mmol), 200 nM biotinylated histone H1, 200 nM sIDNA, and 1 nM PARP enzyme. Auto reactions utilizing SPA bead-based detection were carried out in 100 μl volumes in white 96 well plates. Reactions were initiated by adding 50 μl of 2×$NAD^+$ substrate mixture to 50 μl of 2×enzyme mixture containing PARP and DNA. These reactions were terminated by the addition of 150 μl of 1.5 mM benzamide (~-1000-fold over its IC50). 170 μl of the stopped reaction mixtures were transferred to streptavidin Flash Plates, incubated for 1 hr, and counted using a TopCount microplate scintillation counter. The $K_i$ data was determined from inhibition curves at various substrate concentrations and are shown in Table 1 for representative compounds of the present invention and for non-quaternary compounds. The Table 1 data indicates that quaternary compounds of the present invention have a higher affinity for the PARP enzyme compared to non-quaternary compounds. Table 2 shows $K_i$ data for compounds of the present invention, however, the corresponding non-quaternary compound was not made and thus there is only data in this table for the compounds of the present invention (the $K_i$ values in Table 2 correspond to Examples 45-73).

TABLE 1

Inhibition of PARP

| Compound | PARP Inhibition $K_i$ (nM) |
|---|---|
| 2-(2-methylpyrrolidin-2-yl)-1H-benzimidazole-4-carboxamide | 4.3 |
| 2-[(2R)-pyrrolidin-2-yl]-1H-benzimidazole-4-carboxamide | 8 |
| 2-[(2R)-2-methylpyrrolidin-2-yl]-1H-benzimidazole-4-carboxamide | 5.4 |
| 2-[(2S)-pyrrolidin-2-yl]-1H-benzimidazole-4-carboxamide | 28.4 |
| 2-[(2S)-2-methylpyrrolidin-2-yl]-1H-benzimidazole-4-carboxamide | 5.1 |
| 2-[(2S)-1-methylpyrrolidin-2-yl]-1H-benzimidazole-4-carboxamide | 30.8 |
| 2-[(2R)-1-methylpyrrolidin-2-yl]-1H-benzimidazole-4-carboxamide | 7.3 |
| 2-(1,2-dimethylpyrrolidin-2-yl)-1H-benzimidazole-4-carboxamide | 6.2 |
| 2-[(2S)-1-ethylpyrrolidin-2-yl]-1H-benzimidazole-4-carboxamide | 49 |
| 2-(1-ethyl-2-methylpyrrolidin-2-yl)-1H-benzimidazole-4-carboxamide | 6 |
| 2-[(2S)-1-propylpyrrolidin-2-yl]-1H-benzimidazole-4-carboxamide | 129 |
| 2-[(2R)-1-propylpyrrolidin-2-yl]-1H-benzimidazole-4-carboxamide | 146 |
| 2-(2-methyl-1-propylpyrrolidin-2-yl)-1H-benzimidazole-4-carboxamide | 18.7 |
| 2-[(2R)-1-isopropylpyrrolidin-2-yl]-1H-benzimidazole-4-carboxamide | 12.8 |
| 2-[(2S)-1-isopropylpyrrolidin-2-yl]-1H-benzimidazole-4-carboxamide | 19.3 |
| 2-(1-isopropyl-2-methylpyrrolidin-2-yl)-1H-benzimidazole-4-carboxamide | 17.5 |
| 2-[(2S)-1-cyclobutylpyrrolidin-2-yl]-1H-benzimidazole-4-carboxamide | 338 |
| 2-[(2R)-1-cyclobutylpyrrolidin-2-yl]-1H-benzimidazole-4-carboxamide | 142 |
| 2-(1-cyclobutyl-2-methylpyrrolidin-2-yl)-1H-benzimidazole-4-carboxamide | 31.3 |
| 2-pyrrolidin-3-yl-1H-benzimidazole-4-carboxamide | 3.9 |
| 2-(3-methylpyrrolidin-3-yl)-1H-benzimidazole-4-carboxamide | 3.9 |
| 2-(1-propylpyrrolidin-3-yl)-1H-benzimidazole-4-carboxamide | 8.1 |
| 2-(3-methyl-1-propylpyrrolidin-3-yl)-1H-benzimidazole-4-carboxamide | 4.2 |
| 2-[1-(cyclopropylmethyl)pyrrolidin-3-yl]-1H-benzimidazole-4-carboxamide | 5.2 |
| 2-[1-(cyclopropylmethyl)-3-methylpyrrolidin-3-yl]-1H-benzimidazole-4-carboxamide | 5 |
| 2-(1-isobutylpyrrolidin-3-yl)-1H-benzimidazole-4-carboxamide | 7.4 |
| 2-(1-isobutyl-3-methylpyrrolidin-3-yl)-1H-benzimidazole-4-carboxamide | 3.8 |
| 2-(1-isopropylpyrrolidin-3-yl)-1H-benzimidazole-4-carboxamide | 9.2 |
| 2-(1-isopropyl-3-methylpyrrolidin-3-yl)-1H-benzimidazole-4-carboxamide | 4.4 |

TABLE 1-continued

Inhibition of PARP

| Compound | PARP Inhibition $K_i$ (nM) |
|---|---|
| 2-(1-cyclobutylpyrrolidin-3-yl)-1H-benzimidazole-4-carboxamide | 6.8 |
| 2-(1-cyclobutyl-3-methylpyrrolidin-3-yl)-1H-benzimidazole-4-carboxamide | 4 |
| 2-(1-cyclopentylpyrrolidin-3-yl)-1H-benzimidazole-4-carboxamide | 5.5 |
| 2-(1-cyclopentyl-3-methylpyrrolidin-3-yl)-1H-benzimidazole-4-carboxamide | 3.4 |
| 2-(1-cyclohexylpyrrolidin-3-yl)-1H-benzimidazole-4-carboxamide | 7 |
| 2-(1-cyclohexyl-3-methylpyrrolidin-3-yl)-1H-benzimidazole-4-carboxamide | 5.8 |
| 2-(1-tetrahydro-2H-pyran-4-ylpyrrolidin-3-yl)-1H-benzimidazole-4-carboxamide | 8.2 |
| 2-(3-methyl-1-tetrahydro-2H-pyran-4-ylpyrrolidin-3-yl)-1H-benzimidazole-4-carboxamide | 7.2 |
| 2-[1-(pyridin-4-ylmethyl)pyrrolidin-3-yl]-1H-benzimidazole-4-carboxamide | 14.2 |
| 2-[3-methyl-1-(pyridin-4-ylmethyl)pyrrolidin-3-yl]-1H-benzimidazole-4-carboxamide | 8.9 |
| 2-[1-(2-phenylethyl)pyrrolidin-3-yl]-1H-benzimidazole-4-carboxamide | 9.1 |
| 2-[3-methyl-1-(2-phenylethyl)pyrrolidin-3-yl]-1H-benzimidazole-4-carboxamide | 10.5 |
| 2-[1-(1-methyl-3-phenylpropyl)pyrrolidin-3-yl]-1H-benzimidazole-4-carboxamide | 13.2 |
| 2-[3-methyl-1-(1-methyl-3-phenylpropyl)pyrrolidin-3-yl]-1H-benzimidazole-4-carboxamide | 12 |
| 2-azetidin-2-yl-1H-benzimidazole-4-carboxamide | 34 |
| 2-(2-methylazetidin-2-yl)-1H-benzimidazole-4-carboxamide | 14.1 |
| 2-(1-isopropylazetidin-2-yl)-1H-benzimidazole-4-carboxamide | 118 |
| 2-(1-isopropyl-2-methylazetidin-2-yl)-1H-benzimidazole-4-carboxamide | 41.6 |
| 2-(1-cyclobutylazetidin-2-yl)-1H-benzimidazole-4-carboxamide | 80 |
| 2-(1-cyclobutyl-2-methylazetidin-2-yl)-1H-benzimidazole-4-carboxamide | 33.3 |
| 2-(1-cyclopentylazetidin-2-yl)-1H-benzimidazole-4-carboxamide | 176 |
| 2-(1-cyclopentyl-2-methylazetidin-2-yl)-1H-benzimidazole-4-carboxamide | 31.1 |
| 2-(1-cyclohexylazetidin-2-yl)-1H-benzimidazole-4-carboxamide | 245 |
| 2-(1-cyclohexyl-2-methylazetidin-2-yl)-1H-benzimidazole-4-carboxamide | 27.7 |
| 2-azetidin-3-yl-1H-benzimidazole-4-carboxamide | 6 |
| 2-(3-methylazetidin-3-yl)-1H-benzimidazole-4-carboxamide | 4.4 |
| 2-(1-propylazetidin-3-yl)-1H-benzimidazole-4-carboxamide | 14.1 |
| 2-(3-methyl-1-propylazetidin-3-yl)-1H-benzimidazole-4-carboxamide | 6.9 |
| 2-[1-(cyclopropylmethyl)azetidin-3-yl]-1H-benzimidazole-4-carboxamide | 19 |
| 2-[1-(cyclopropylmethyl)-3-methylazetidin-3-yl]-1H-benzimidazole-4-carboxamide | 8 |
| 2-(1-isobutylazetidin-3-yl)-1H-benzimidazole-4-carboxamide | 14.4 |
| 2-(1-isobutyl-3-methylazetidin-3-yl)-1H-benzimidazole-4-carboxamide | 5.6 |
| 2-(1-cyclobutylazetidin-3-yl)-1H-benzimidazole-4-carboxamide | 16.4 |
| 2-(1-cyclobutyl-3-methylazetidin-3-yl)-1H-benzimidazole-4-carboxamide | 6.1 |
| 2-(1-cyclopentylazetidin-3-yl)-1H-benzimidazole-4-carboxamide | 14 |
| 2-(1-cyclopentyl-3-methylazetidin-3-yl)-1H-benzimidazole-4-carboxamide | 4 |
| 2-(1-cyclohexylazetidin-3-yl)-1H-benzimidazole-4-carboxamide | 16 |
| 2-(1-cyclohexyl-3-methylazetidin-3-yl)-1H-benzimidazole-4-carboxamide | 5.6 |
| 2-(1-tetrahydro-2H-pyran-4-ylazetidin-3-yl)-1H-benzimidazole-4-carboxamide | 45.6 |
| 2-(3-methyl-1-tetrahydro-2H-pyran-4-ylazetidin-3-yl)-1H-benzimidazole-4-carboxamide | 12.7 |
| 2-{1-[(dimethylamino)sulfonyl]azetidin-3-yl}-1H-benzimidazole-4-carboxamide | 16 |
| 2-{1-[(dimethylamino)sulfonyl]-3-methylazetidin-3-yl}-1H-benzimidazole-4-carboxamide | 7 |
| 2-[(2S)-piperidin-2-yl]-1H-benzimidazole-4-carboxamide | 46.1 |
| 2-[(2R)-piperidin-2-yl]-1H-benzimidazole-4-carboxamide | 47.4 |
| 2-[piperidin-2-yl]-1H-benzimidazole-4-carboxamide | 32.2 |
| 2-(2-methylpiperidin-2-yl)-1H-benzimidazole-4-carboxamide | 4.6 |
| 2-(1-propylpiperidin-2-yl)-1H-benzimidazole-4-carboxamide | 120 |
| 2-(2-methyl-1-propylpiperidin-2-yl)-1H-benzimidazole-4-carboxamide | 18.7 |
| 2-{1-[(dimethylamino)sulfonyl]piperidin-4-yl}-1H-benzimidazole-4-carboxamide | 31.1 |
| 2-{1-[(dimethylamino)sulfonyl]-4-methylpiperidin-4-yl}-1H-benzimidazole-4-carboxamide | 8.8 |
| 2-(1-cyclobutylpiperidin-4-yl)-1H-benzimidazole-4-carboxamide | 6.3 |
| 2-(1-cyclobutyl-4-methylpiperidin-4-yl)-1H-benzimidazole-4-carboxamide | 9.2 |
| 2-(1-isopropylpiperidin-4-yl)-1H-benzimidazole-4-carboxamide | 6 |
| 2-(1-isopropyl-4-methylpiperidin-4-yl)-1H-benzimidazole-4-carboxamide | 8 |
| 2-(1-propylpiperidin-4-yl)-1H-benzimidazole-4-carboxamide | 8.6 |
| 2-(4-methyl-1-propylpiperidin-4-yl)-1H-benzimidazole-4-carboxamide | 13.5 |
| 2-azepan-4-yl-1H-benzimidazole-4-carboxamide | 5.7 |
| 2-(4-methylazepan-4-yl)-1H-benzimidazole-4-carboxamide | 3.3 |
| 2-(1-cyclopentylazepan-4-yl)-1H-benzimidazole-4-carboxamide | 3.9 |
| 2-(1-cyclopentyl-4-methylazepan-4-yl)-1H-benzimidazole-4-carboxamide | 7.3 |
| 2-(1-cyclohexylazepan-4-yl)-1H-benzimidazole-4-carboxamide | 4.8 |
| 2-(1-cyclohexyl-4-methylazepan-4-yl)-1H-benzimidazole-4-carboxamide | 11.9 |
| 2-[(2R)-2-methyl-5-oxopyrrolidin-2-yl]-1H-benzimidazole-4-carboxamide | 29 |
| 2-[(2R)-5-oxopyrrolidin-2-yl]-1H-benzimidazole-4-carboxamide | 16 |

TABLE 2

Inhibition of PARP $K_i$ (nM)

| | | | | | | | |
|---|---|---|---|---|---|---|---|
| 8.6 | 10.9 | 1.8 | 3.1 | 172 | 6.7 | 3.4 | 4.3 |
| 8.4 | 44.9 | 4175 | 14.9 | 26.4 | 24.4 | 11.1 | 8.1 |
| 5.1 | 422 | 9.2 | 5.5 | 52 | 24.8 | 2.4 | 4.5 |
| 4656 | 341 | 9.6 | 9.7 | | | | |

Cellular PARP Assay:

C41 cells were treated with a compound of the present invention for 30 minutes in 96 well plate. PARP was then activated by damaging DNA with 1 mM $H_2O_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10 H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$ for representative compounds of the present invention are provided in Table 3.

TABLE 3

| Cellular Activity $EC_{50}$ (nM) | | | | |
|---|---|---|---|---|
| 5.5 | 9.3 | 6.3 | 2.2 | 26 |
| 0.8 | 1.1 | 1.3 | 2.2 | 2.4 |
| 5.0 | 32.6 | 1.0 | 2.3 | 1.9 |
| 14 | 12.6 | 29.0 | 137 | 4.8 |
| 1.6 | 4.3 | 16.1 | 2.8 | 6.1 |
| 13.3 | 21.0 | 2.0 | 12.5 | 12.7 |
| 5.2 | 3.2 | 3.5 | 3.5 | 2.8 |
| 31 | 3.9 | 7.9 | 590 | 10.9 |
| 2.7 | 1.2 | 1.5 | 53 | 8.8 |
| 5.8 | 6.7 | 9.8 | 15 | 1 |

Deaths Following Lipopolysaccharide (LPS) Challenge

Female BALB/c mice were dosed orally, twice a day with vehicle (0.2% HPMC), or drug at 30 mg/kg/day or 100 mg/kg/day. The mice were injected intravenous with 20 mg/kg LPS at 30 minutes after the first treatment dose. They were monitored for survival for 72 hours or until 80-90% lethality was observed. Table 4 provides lethality data for a representative compound of the present invention and a non-quatemary compound, 2-(1-propylpiperidin-4-yl)-1H-benzimidazole-4-carboxamide.

TABLE 4

| compound | 0 (mg/kg) | 30 (mg/kg) | 100 (mg/kg) |
|---|---|---|---|
| 2-[(2S)-2-methylpyrrolidin-2-yl]-1H-benzimidazole-4-carboxamide | 9/10 | 8/10 | 4/10* |
| 2-(1-propylpiperidin-4-yl)-1H-benzimidazole-4-carboxamide | 8/10 | 8/10 | 9/10 |

*Indicates statistical significace, $p < 0.05$.

Percent Decrease in Inflammatory Cell Influx or IL-1 Levels in the Peritoneum Following Zymosan Challenge Compounds were administered orally before an intraperitoneal zymosan injection (2 mg/animal). Four hours post zymosan injection, the peritoneal cavity was lavaged, and the lavage fluid was measured for cell influx and IL-1 levels. Table 4 provides the percent decrease in cell influx and IL-1 levels relative to control for representative compounds of the present invention and a non-quatemary compound, 2-(1-propylpiperidin-4-yl)-1H-benzimidazole-4-carboxamide. The data indicates the representative compounds of the present invention reduce or prevent inflammation.

TABLE 4

| compound | 0 mg/kg | | 30 mg/kg | | 100 mg/kg | |
|---|---|---|---|---|---|---|
| | Cell Influx | IL-1 level | Cell Influx | IL-1 level | Cell Influx | IL-1 level |
| 2-[(2R)-2-methylpyrrolidin-2-yl]-1H-benzimidazole-4-carboxamide | 0 | 0 | 38% | 55%* | 64%* | 60%* |
| 2-[(2S)-2-methylpyrrolidin-2-yl]-1H-benzimidazole-4-carboxamide | 0 | 0 | 39% | 54%* | 66%* | 65%* |
| 2-(1-propylpiperidin-4-yl)-1H-benzimidazole-4-carboxamide | 0 | 0 | 0 | 32% | 23% | 47%* |

*Indicates statistical significace, $p < 0.05$.

TABLE 3-continued

| Cellular Activity $EC_{50}$ (nM) | | | | |
|---|---|---|---|---|
| 2 | 13.5 | 2 | 13 | 2.4 |
| 7.4 | 5.2 | 3.2 | 8 | 13 |
| 17 | 1.2 | 2 | | |

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing apoptosis of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetaminophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemernann et al., Proc. Natl. Acad. Sci. USA 94 (1997), 679-683 D. Weltin et al. Int. J. Immunopharmacol. 17 (1995), 265-271, H. Kröger et al. Inflammation 20 (1996), 203-215; W. Ehrlich et al. Rheumatol. Int. 15 (1995), 171-172; C. Szabo et al., Proc. NatI. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting the free base of a compound of the present invention with a suitable acid. Representative acids include, but are not limited to acetatic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of the present invention may be administered as a pharmaceutical composition containing a compound of the present invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DBU for 1,8-diazabicyclo [5.4.0]undec-7-ene; DMF for N,N-dimethylformamide; DMSO for dimethylsulfoxide; $Et_2O$ for diethyl ether, EtOAc for ethyl acetate; EtOH for ethanol; HPLC for high pressure liquid chromatography; LDA for lithium diisopropylamide; MeOH for methanol; psi for pounds per square inch; TFA for trifluoroacetic acid; THF for tetrahydrofuran, and TMS for trimethylsilane.

The following Examples are intended as an illustration of and not a limitation upon the scope of the invention as defined in the appended claims. The compounds of this invention can be prepared by a variety of synthetic routes.

EXAMPLE 1

2-(2-methylpyrrolidin-2-yl)-1H-benzimidazole-4-carboxamide

EXAMPLE 1A 1-benzyl 2-methyl 2-methylpyrrolidine-1,2-dicarboxylate

A solution of 1-benzyl 2-methyl pyrrolidine-1,2-dicarboxylate (15.0 g, 57 mmol) and iodomethane (7.11 ml, 114 mmol) in THF (100 mL) was treated with NaN(TMS)$_2$ (1.0 M solution in THF, 114 mL, 114 mmol) at −75° C. under nitrogen. The temperature of the cooling bath was then slowly raised to −20° C. within 1 h and the mixture was stirred at the same temperature for another 3 h. After quenching with water, the mixture was acidified with 2 N HCl (~100 mL) and was partitioned between water (400 mL) and EtOAc (400 mL). The organic phase was washed with brine and concentrated. The residue was purified by flash column chromatography (silica gel, EtOAc/hexane) to give Example 1A (15.15 g, Yield: 96%). MS (DCI/NH$_3$) m/z 278 (M+H)$^+$.

EXAMPLE 1B

1-[(benzyloxy)carbonyl]-2-methylpyrrolidine-2-carboxylic acid

A solution of Example 1A (15.15 g, 54.63 mmol) in a mixture of THF (100 mL) and water (50 mL) was treated with LiOH.H$_2$O (4.58 g, 109.26 mmol) in water (50 mL). Methanol was added until a transparent solution formed (60 mL). This solution was heated at 60° C. for overnight and the organic solvents were removed under vacuum. The residual aqueous solution was acidified with 2 N HCl to pH 2 and was partitioned between ethyl acetate and water. The organic phase was washed with water, dried (MgSO$_4$), filtered and concentrated to give Example 1B as a white solid (13.72 g, 95.4% yield). MS (DCI/NH$_3$) m/z 264 (M+H)$^+$.

EXAMPLE 1C benzyl 2-({[2-amino-3-(aminocarbonyl)phenyl]amino}carbonyl)-2-methylpyrrolidine-1-carboxylate A solution of Example 1B (13.7 g, 52 mmol) in a mixture of pyridine (60 mL) and DMF (60 mL) was treated with 1,1'-carbonyldiimidazole (9.27 g, 57.2 mmol) at 45° C. for 2 h. 2,3-Diamino-benzamide dihydrochloride (11.66 g, 52 mmol), which was synthesized as described in previous patent application WO0026192, was added and the mixture was stirred at rt overnight. After concentration under vacuum, the residue was partitioned between ethyl acetate and diluted sodium bicarbonate aqueous solution. The slightly yellow solid material was collected by filtration, washed with water and ethyl acetate, and dried to give Example 1C (16.26 g). Extraction of the aqueous phase with ethyl acetate followed by concentration, filtration and water-EtOAc wash, provided additional 1.03 g of Example 1C. Combined yield: 84%. MS (APCI) m/z 397 (M+H)$^+$.

EXAMPLE 1D benzyl 2-[4-(aminocarbonyl)-1H-benzimidazol-2-yl]-2-methylpyrrolidine-1-carboxylate A suspension of Example 1C (17.28 g, 43.6 mmol) in acetic acid (180 mL) was heated under reflux for 2 h. After cooling, the solution was concentrated and the residual oil was partitioned between ethyl acetate and sodium bicarbonate aqueous solution. The organic phase was washed with water and concentrated. The residue was purified by flash column chromatography (silica gel, 3-15% CH$_3$OH in 2:1 EtOAc/hexane) to provide Example 1D (16.42 g, Yield: 99%).

MS (APCI) m/z 379 (M+H)$^+$.

EXAMPLE 1E 2-(2-methylpyrrolidin-2-yl)-1H-benzimidazole-4-carboxamide

A solution of Example 1D (15.0 g, 40 mmol) in methanol (250 ml) was treated with 10% Pd/C (2.8 g) under 60 psi of hydrogen for overnight. Solid material was filtered off and the filtrate was concentrated. The residual solid was recrystallized in methanol to give 7.768 g of Example 1E as free base. The bis-HCl salt was prepared by dissolving the free base in warm methanol and treating with 2 equivalents of HCl in ether (10.09 g). MS (APCI) m/z 245 (M+H)$^+$; $^1$H NMR (500 MHz, D$_2$O): δ 1.92 (s, 3 H), 2.00-2.09 (m, 1 H), 2.21-2.29 (m, 1 H), 2.35-2.41 (m, 1 H), 2.52-2.57 (m, 1 H), 3.54-3.65 (m, 2 H), 7.31 (t, J=7.93 Hz, 1 H), 7.68 (dd, J=8.24, 0.92 Hz, 1 H), 7.72 (dd, J=7.63, 0.92 Hz, 1 H); Anal. Calcd for C$_{13}$H$_{16}$N$_4$O.2 HCl: C, 49.22; H, 5.72N, 17.66. Found: C, 49.30; H, 5.60; N, 17.39.

EXAMPLE 3

2-[(2R)-2-methylpyrrolidin-2-yl]-1H-benzimidazole-4-carboxamide

EXAMPLE 3A benzyl(2R)-2-[4-(aminocarbonyl)-1H-benzimidazol-2-yl]-2-methylpyrrolidine-1-carboxylate Example 1D (1.05 g, 2.8 mmol) was resolved on chiral HPLC (Chiralcel OD, 80/10/10 hexane/EtOH/MeOH). The faster eluting peak was collected and concentrated to provide Example 3A (99.4% e.e., 500 mg). MS (APCI) m/z 379 (M+H)$^+$.

EXAMPLE 3B

2-[(2R)-2-methylpyrrolidin-2-yl]-1H-benzimidazole-4-carboxamide

A solution of Example 3A (500 mg, 1.32 mmol) in methanol (10 ml) was treated with 10% Pd/C (150 mg) under hydrogen for overnight (balloon). Solid material was filtered off and the filtrate was concentrated. The residual solid was further purified by HPLC (Zorbax C-18, CH$_3$CN/H$_2$O/0.1%TFA) and was converted to bis-HCl salt to provide Example 4 as white solid (254 mg). Co-crystallization of the free base with 1 equivalent of L-tartaric acid in methanol gave a single crystal that was suitable for X-ray study. The X-ray structure with L-tartaric acid was assigned the R-configuration. MS (APCI) m/z 245 (M+H)$^+$; $^1$H NMR (500 MHz, D$_2$O): δ 2.00 (s, 3 H), 2.10-2.19 (m, 1 H), 2.30-2.39 (m, 1 H), 2.45-2.51 (m, 1 H), 2.61-2.66 (m, 1 H), 3.64-3.73 (m, 2 H), 7.40 (t, J=7.95 Hz, 1 H), 7.77 (d, J=8.11 Hz, 1 H), 7.80 (d,

EXAMPLE 4 (A-861696)

2-[(2S)-2-methylpyrrolidin-2-yl]-1H-benzimidazole-4-carboxamide

Example 4 was prepared as in Example 3 by chiral separation of Example 1D followed by hydrogenation. MS (APCI) m/z 245 (M+H)+; $^1$H NMR (500 MHz, $D_2O$): δ 1.99 (s, 3 H), 2.09-2.19 (m, 1 H), 2.30-2.38 (m, 1 H), 2.44-2.50 (m, 1 H), 2.61-2.66 (m, 1 H), 3.63-3.73 (m, 2 H), 7.40 (t, J=7.95 Hz, 1 H), 7.77 (dd, J=8.11, 0.94 Hz, 1 H), 7.81 (dd, J=7.80, 0.94 Hz, 1 H); Anal. Calcd for $C_{13}H_{16}N_4O.2$ HCl: C, 49.22; H, 5.72; N, 17.66. Found: C, 49.27; H, 5.60; N, 17.61.

EXAMPLE 5

2-(1,2-dimethylpyrrolidin-2-yl)-1H-benzimidazole-4-carboxamide

A solution of the free base of Example 1E (300 mg, 1.22 mmol) in methanol (20 mL) was treated with formaldehyde (37 wt % in water, 228 μL, 3.07 mmol) at room temperature for overnight. Sodium cyanoborohydride (193 mg, 3.07 mmol) was then added and the solution was stirred at rt for 3 h. After concentration under reduced pressure, the residue was dissolved in a mixture of trifluoroacetic acid and water and was purified by HPLC (Zorbax C-8, 0.1% TFA/$CH_3CN$/$H_2O$). The title compound as the TFA salt was converted to its HCl salt by dissolving in methanol and treating with HCl in ether (317 mg, 91%). MS (APCI) m/z 259 (M+H)+; $^1$H NMR (400 MHz, $D_2O$): δ 1.94 (s, 3 H), 2.25-2.43 (m, 2 H), 2.49-2.56 (m, 1 H), 2.61-2.68 (m, 1 H), 2.91 (br s, 3 H), 3.49-3.61 (m, 1 H), 3.79-3.99 (m, 1 H), 7.40 (t, J=7.98 Hz, 1 H), 7.76 (d, J=8.29 Hz, 1 H), 7.82 (d, J=7.67 Hz, 1 H); Anal. Calcd for $C_{14}H_{14}N_4O.1.7$ HCl; C, 52.50; H, 6.20; N, 17.49. Found: C, 52.37; H, 6.10; N, 17.42.

EXAMPLE 6

2-(1-ethyl-2-methylpyrrolidin-2-yl)-1H-benzimidazole-4-carboxamide

The title compound was prepared according to the procedure for Example 5, substituting acetadehyde for formaldehyde. MS (APCI) m/z 273 (M+H)+; $^1$H NMR (400 MHz, $D_2O$): δ 1.26-1.36 (m, 3 H), 1.93 (br s, 3 H), 2.32-2.44 (m, 2 H), 2.45-2.56 (m, 2 H), 3.19-3.27 (m, 1 H), 3.41-3.52 (m, 1 H), 3.64-3.72 (m, 1 H), 3.98-4.09 (m, 1 H), 7.43 (t, J=7.83 Hz, 1 HZ, 1 H), 7.80 (d, J=7.98 Hz, 1 H), 7.86 (d, J=7.36 Hz, 1 H); Anal. Calcd for $C_{15}H_{20}N_4O.2$ HCl: C, 52.18; H, 6.42; N, 16.23. Found: C, 52.47; H, 6.44; N, 16.69.

EXAMPLE 7

2-(2-methyl-1-propylpyrrolidin-2-yl)-1H-benzimidazole-4-carboxamide

The title compound was prepared according to the procedure for Example 5, substituting propionaldehyde for formaldehyde. MS (APCI) m/z 287 (M+H)+; $^1$H NMR (400 MHz, $D_2O$): δ 0.94 (t, J=7.36 Hz, 3 H), 1.64-1.81 (m, 3 H), 1.94 (s, 3 H), 2.29-2.45 (m, 2 H), 2.48-2.57 (m, 2 H), 3.10-3.19 (m, 1 H), 3.47-3.62 (m, 1 H), 3.91-4.06 (m, 1 H), 7.42 (t, J=7.98 Hz, 1 H), 7.79 (d, J=7.98 Hz, 1 H), 7.85 (d, J=7.67 Hz, 1 H); Anal. Calcd for $C_{16}H_{22}N_4O.2.5$ HCl: C, 50.90, H, 6.54; N, 14.84. Found: C, 50.86; H, 6.80; N, 14.67.

EXAMPLE 8

2-(1-isopropyl-2-methylpyrrolidin-2-yl)-1H-benzimidazole-4-carboxamide

The title compound was prepared according to the procedure for Example 5, substituting acetone for formaldehyde. MS (APCI) m/z 287 (M+H)+; $^1$H NMR (400 MHz, $D_2O$): δ 0.89 (d, J=4.91 Hz, 3 H), 1.42 (br s, 3 H), 2.01 (br s, 3 H), 2.34 (m, 2 H), 2.43-2.53 (m, 1 H), 2.55-2.65 (m, 1 H), 3.54-3.63 (m, 1 H), 3.71 (m, 1 H), 3.97-4.07 (m, 1 H), 7.43 (t, J=7.67 Hz, 1 H), 7.81 (d, J=7.98 Hz, 1 H), 7.87 (d, J=7.67 Hz, 1 H); Anal. Calcd for $C_{16}H_{22}N_4O.2.7$ HCl: C, 49.94 H, 6.47; N, 14.56. Found: C, 50.00; H, 6.30; N, 13.69.

EXAMPLE 9

2-(1-cyclobutyl-2-methylpyrrolidin-2-yl)-1H-benzimidazole-4-carboxamide

The title compound was prepared according to the procedure for Example 5, substituting cyclobutanone for formaldehyde. MS (APCI) m/z 299 (M+H)+; $^1$H NMR (400 MHz, $D_2O$): δ 1.60-1.70 (m, 3 H), 1.78-1.84 (m, 1 H), 1.97 (br s, 3 H), 2.08-2.16 (m, 1 H), 2.24-2.38 (m, 3 H), 2.45 (ddd, J=13.50, 6.75, 6.75 Hz, 1 H), 2.85 (q, J=8.90 Hz, 1 H), 3.44-3.53 (m, 1 H), 3.69-3.85 (m, 2 H), 7.43 (t, J=7.98 Hz, 1 H), 7.79 (d, J=7.98 Hz, 1 H), 7.86 (d, J=7.67 Hz, 1 H); Anal. Calcd for $C_{17}H_{22}N_4O.2.8$ HCl: C, 50.99; H, 6.24; N, 13.99. Found: C, 51.00; H, 6.40; N, 13.52.

EXAMPLE 10

2-(3-methylpyrrolidin-3-yl)-1H-benzimidazole-4-carboxamide

EXAMPLE 10A 1-benzyl 3-methyl 3-methylpyrrolidine-1,3-dicarboxylate

A solution of 1-benzyl 3-methyl pyrrolidine-1,3-dicarboxylate (4.0 g, 15.2 mmol) and iodomethane (2.0 ml) in THF (50 mL) was treated with $NaN(TMS)_2$ in THF (1.0 M, 32 mL, 32 mmol) at −70° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and concentrated. The residue was purified by flash column chromatography to give Example 10A (4.1 g, 97%). MS ($DCI/NH_3$) m/z 278 (M+H)+.

EXAMPLE 10B

1-[(benzyloxy)carbonyl]-3-methylpyrrolidine-3-carboxylic acid

A solution of Example 10A (4.1 g, 14.8 mmol) in a mixture of THF (20 mL) and water (30 mL) was treated with $LiOH.H_2O$ (0.93 g, 22.2 mmol) in water (10 mL). Methanol was added until a transparent solution formed (20 mL). This solution was heated at 60° C. for overnight and the organic solvents were removed under vacuum. The residual aqueous solution was acidified with 2N HCl to pH 2 and was partitioned between ethyl acetate and water. The organic phase was washed with water, dried (MgSO$_4$), filtered and concentrated to give Example 10B as a white solid (3.8 g, 97% yield). MS (DCI/NH$_3$) m/z 264 (M+H)$^+$.

EXAMPLE 10C benzyl 3-({[2-amino-3-(aminocarbonyl)phenyl]amino}carbonyl)-3-methylpyrrolidine-1-carboxylate A solution of Example 10B (1.0 g, 3.8 mmol) in a mixture of pyridine (10 mL) and DMF (10 mL) was treated with 1,1'-carbonyldiimidazole (0.74 g, 4.6 mmol) at 45° C. for 2 h. 2,3-Diamino-benzamide dihydrochloride (0.9 g, 3.8 mmol) was added and the mixture was stirred at rt overnight. After concentration under vacuum, the residue was partitioned between ethyl acetate and diluted sodium bicarbonate aqueous solution. The formed slightly yellow solid material was collected by filtration, washed with water and ethyl acetate, and dried to give Example 1C (1.2 g). Yield: 80%. MS (APCI) m/z 397 (M+H)$^+$.

EXAMPLE 10D benzyl 3-[4-(aminocarbonyl)-1H-benzimidazol-2-yl]-3-methylpyrrolidine-1-carboxylate A suspension of Example 10C (1.2 g, 3.0 mmol) in acetic acid (50 mL) was heated under reflux for 2 h. After cooling, the solution was concentrated and the residual oil was partitioned between ethyl acetate and sodium bicarbonate aqueous solution. The organic phase was washed with water and concentrated. The residue was purified by flash column chromatography to provide Example 10D (1.1 g, Yield: 99%). MS (APCI) m/z 379 (M+H)$^+$.

EXAMPLE 10E 2-(3-methylpyrrolidin-3-yl)-1H-benzimidazole-4-carboxamide

A solution of Example 10D (1.1 g, 2.9 mmol) in methanol (50 ml) was treated with 10% Pd/C (100 mg) under hydrogen overnight. Solid material was filtered off and the filtrate was concentrated. The residual solid was re-crystallized in methanol to give 0.5 g of Example 10E. Yield: 71%. MS (APCI) m/z 245 (M+H)$^+$; $^1$H NMR (500 MHz, CD$_3$O): δ 1.73 (s, 3 H), 2.29-2.36 (m, 1 H), 2.69-2.76 (m, 1 H), 3.40-3.48 (m, 2 H), 3.55-3.62 (m, 1 H), 4.21 (d, J=11.90 Hz, 1 H), 7.38 (t, J=7.78 Hz, 1 H), 7.73 (d, J=7.93 Hz, 1 H), 7.94 (d, J=6.71 Hz, 1 H); Anal. Calcd for C$_{13}$H$_{16}$N$_4$O.2.0 TFA: C, 45.29; H, 4.04; N, 13.20. Found: C, 45.14; H, 3.99; N, 12.55.

EXAMPLE 11

2-(3-methyl-1-propylpyrrolidin-3-yl)-1H-benzimidazole-4-carboxamide

A solution of the free base of Example 10E (70 mg, 0.3 mmol) in methanol (5 mL) was treated with propionaldehyde (25 mg, 0.4 mmol) at room temperature overnight. Sodium triacetoxyborohydride (254 mg, 1.2 mmol) was then added and the solution was stirred at rt for 3 h. After concentration under vacuum, the residue was separated by HPLC (Zorbax C-8, 0.1% TFA/CH$_3$CN/H$_2$O) to give 55 mg of desired product. Yield: 35%. MS (APCI) m/z 287 (M+H)$^+$; $^1$H NMR (500 MHz, CD$_3$O): δ 0.89 (t, J=7.33 Hz, 2 H), 1.60 (s, 3 H), 1.63-1.77 (m, 2 H), 2.12-2.40 (m, 1 H), 2.59-2.73 (m, 1 H), 3.03-3.40 (m, 5 H), 3.69 (s, 1 H), 3.96-4.50 (m, 1 H), 7.21 (t, 1 H), 7.56 (s, 1 H), 7.76 (s, 1 H); Anal. Calcd for C$_{16}$H$_{22}$N$_4$O.2.0 TFA: C, 46.70; H, 4.70; N, 10.89. Found: C, 46.89; H, 4.68; N, 10.98.

EXAMPLE 12

2-[1-(cyclopropylmethyl)-3-methylpyrrolidin-3-yl]-1H-benzimidazole-4-carboxamide The title compound was prepared according to the procedure for Example 11, substituting cyclopropyl acetadehyde for propionaldehyde. MS (APCI) m/z 299 (M+H)$^+$; $^1$H NMR (500 MHz, CD$_3$OD): δ 0.43-0.52 (m, 2 H), 0.77 (d, J=7.18 Hz, 2 H), 1.13-1.24 (m, 2 H), 1.76 (s, 3 H), 2.30-2.56 (m, J=21.53 Hz, 1 H), 2.77-2.89 (m, 1 H), 3.23 (s, 2 H), 3.30-3.59 (m, 1 H), 3.79-3.97 (m, 1 H), 4.15-4.73 (m, J=218.06 Hz, 1 H), 7.37 (t, J=7.96 Hz, 1 H), 7.73 (d, J=8.11 Hz, 1 H), 7.92 (d, J=7.80 Hz, 1 H); Anal. Calcd for C$_{17}$H$_{22}$N$_4$O.2 TFA: C, 47.91; H, 4.60; N, 10.64 Found: C, 47.88; H, 6.40; N, 10.23.

EXAMPLE 13

2-(1-isobutyl-3-methylpyrrolidin-3-yl)-1H-benzimidazole-4-carboxamide

The title compound was prepared according to the procedure for Example 11, substituting 2-methylpropanal for propionaldehyde. MS (APCI) m/z 301 (M+H)$^+$; $^1$H NMR (500 MHz, CD$_3$OD): δ 1.08 (d, J=6.55 Hz, 6 H), 1.08-1.17 (m, 1 H), 1.78 (s, 3 H), 2.09-2.23 (m, 1 H), 2.27-2.54 (m, 1 H), 2.68-2.85 (m, 1 H), 3.12-3.24 (m, 2 H), 3.28-3.57 (m, 1 H), 3.72-3.95 (m, 1 H), 4.20-4.70 (m, 1 H), 7.34-7.40 (m, 1 H), 7.72 (d, J=8.11 Hz, 1 H), 7.93 (d, J=7.18 Hz, 1 H); Anal. Calcd for C$_{17}$H$_{24}$N$_4$O.2.5 TFA: C, 45.92; H, 4.55; N, 9.74. Found: C, 46.39; H, 4.67; N, 10.03.

EXAMPLE 14

2-(1-isopropyl-3-methylpyrrolidin-3-yl)-1H-benzimidazole-4-carboxamide

The title compound was prepared according to the procedure for Example 11 substituting acetone for propionaldehyde. MS (APCI) m/z 287 (M+H)$^+$; $^1$H NMR (500 MHz, CD$_3$OD): δ 1.43 (d, J=5.93 Hz, 6 H), 1.78 (s, 3 H), 2.29-2.48 (m, J=34.94 Hz, 1 H), 2.72-2.91 (m, 1 H), 3.33-3.66 (m, 3 H), 3.69-3.92 (m, 1 H), 4.17-4.57 (m, J=121.98 Hz, 1 H), 7.37 (t, J=7.80 Hz, 1 H), 7.73 (d, J=7.80 Hz, 1 H), 7.92 (d, J=7.18 Hz, 1 H); Anal. Calcd for C$_{16}$H$_{22}$N$_4$O.2.4 TFA: C, 45.03; H, 4.53; N, 10.50. Found: C, 45.49; H, 4.50; N, 10.41.

EXAMPLE 15

2-(1-cyclobutyl-3-methylpyrrolidin-3-yl)-1H-benzimidazole-4-carboxamide

The title compound was prepared according to the procedure for Example 11 substituting cyclobutanone for propionaldehyde. MS (APCI) m/z 299 (M+H)$^+$; $^1$H NMR (500 MHz, CD$_3$OD): δ 1.73 (s, 3 H), 1.82-2.01 (m, 2 H), 2.18-2.33 (m, 2 H), 2.38 (s, 3 H), 2.75-2.85 (m, 1 H), 3.14-3.26 (m, J=1.53 Hz, 1 H), 3.33-3.69 (m, 1 H), 3.69-3.84 (m, 1 H), 3.92-4.01 (m, 1 H), 4.04-4.54 (m, 1 H), 7.37 (t, J=7.78 Hz, 1 H), 7.72 (d, J=7.93 Hz, 1 H), 7.93 (d, J=7.32 Hz, 1 H), Anal.

EXAMPLE 16

2-(1-cyclopentyl-3-methylpyrrolidin-3-yl)-1H-benz-
imidazole-4-carboxamide

The title compound was prepared according to the procedure for Example 11, substituting cyclopentanone for propionaldehyde. MS (APCI) m/z 313 (M+H)$^+$; $^1$H NMR (500 MHz, CD$_3$OD): δ 1.73 (s, 3 H), 1.61-1.94 (m, 7 H), 2.20 (s, 2 H), 2.29-2.54 (m, J=58.59 Hz, 1 H), 2.74-2.96 (m, 1 H), 3.28-3.63 (m, 3 H), 3.67-3.95 (m, 3 H), 4.16-4.63 (m, J=160.20 Hz, 1 H), 7.37 (t, J=7.93 Hz, 1 H), 7.73 (d, J=7.93 Hz, 1 H), 7.92 (d, J=6.71 Hz, 1 H); Anal. Calcd for C$_{18}$H$_{24}$N$_4$O.1.7 TFA: C, 50.22; H, 5.12; N, 11.38. Found: C, 51.48; H, 5.12; N, 11.01.

EXAMPLE 17

2-(1-cyclohexyl-3-methylpyrrolidin-3-yl)-1H-benz-
imidazole-4-carboxamide

The title compound was prepared according to the procedure for Example 11, substituting cyclohexanone for propionaldehyde. MS (APCI) m/z 327 (M+H)$^+$; $^1$H NMR (500 MHz, CD$_3$OD): δ 1.73 (s, 3 H), 1.25 (t, J=12.36 Hz, 1 H), 1.30-1.57 (m, 4 H), 1.68-1.81 (m, 4 H), 1.84-2.02 (m, 2 H), 2.11-2.52 (m, 3 H), 2.80 (s, 1 H), 3.21-3.48 (m, 2 H), 3.49-3.78 (m, J=8.24 Hz, 1 H), 3.72-3.89 (m, 1 H), 4.24-4.59 (m, J=113.36, 11.14 Hz, 1 H), 7.37 (t, J=7.78 Hz, 1 H), 7.73 (d, J=7.93 Hz, 1 H), 7.93 (s, 1 H); Anal. Calcd for C$_{19}$H$_{25}$N$_4$O.1.7: C, 52.28; H, 5.18; N, 11.08. Found: C, 52.08; H, 5.32; N, 11.59.

EXAMPLE 18

2-(3-methyl-1-tetrahydro-2H-pyran-4-ylpyrrolidin-3-
yl)-1H-benzimidazole-4-carboxamide The title compound was prepared according to the procedure for Example 11 substituting tetrahydro-4H-pyran-4-one for propionaldehyde. MS (APCI) m/z 329 (M+H)$^+$; $^1$H NMR (500 MHz, CD$_3$OD): δ 1.75 (s, 3 H), 1.74-1.89 (m, 2 H), 2.04-2.21 (m, J=11.54 Hz, 2 H), 2.31-2.48 (m, 1 H), 2.75-2.93 (m, 1 H), 3.39-3.50 (m, 3 H), 3.49-3.60 (m, 2 H), 3.61-3.90 (m, 1 H), 4.06 (d, 2 H), 4.26-4.59 (m, 1 H), 7.37 (t, J=7.80 Hz, 1 H), 7.73 (d, J=7.80 Hz, 1 H), 7.93 (d, J=7.49 Hz, 1 H); Anal. Calcd for C$_{18}$H$_{24}$N$_4$O2.1.7 TFA: C, 41.13; H, 5.28; N, 11.29. Found: C, 41.58; H, 5.30; N, 11.55.

EXAMPLE 19

2-[3-methyl-1-(pyridin-4-ylmethyl)pyrrolidin-3-yl]-
1H-benzimidazole-4-carboxamide The title compound was prepared according to the procedure for Example 11, substituting isonicotinaldehyde for propionaldehyde. MS (APCI) m/z 336 (M+H)$^+$; $^1$H NMR (500 MHz, CD$_3$OD): δ 1.78 (s, 3 H), 2.34-2.48 (m, 1 H), 2.66-2.79 (m, 1 H), 3.34-3.49 (m, 2 H), 3.49-3.60 (m, 1 H), 4.16 (d, 1 H), 4.60 (dd, 2 H), 7.47 (t, 1 H), 7.80 (d, J=7.32 Hz, 1 H), 7.96 (d, 7.63 Hz, 1 H), 8.12 (d, J =6.41 Hz, 2 H), 8.86 (d, J=6.41 Hz, 2 H); Anal. Calcd for C$_{19}$H$_{21}$N$_5$O.2 TFA: C, 49.03; H, 4.11; N, 12.43. Found: C, 49.54; H, 4.08; N, 11.97.

Calcd for C$_{17}$H$_{22}$N$_4$O.1.7 TFA: C, 50.21; H, 4.85; N, 11.71. Found: C, 51.16; H, 4.97; N, 11.62

EXAMPLE 20

2-[3-methyl-1-(2-phenylethyl)pyrrolidin-3-yl]-1H-
benzimidazole-4-carboxamide

The title compound was prepared according to the procedure for Example 11 substituting phenylacetaldehyde for propionaldehyde. MS (APCI) m/z 349 (M+H)$^+$; $^1$H NMR (400 MHz, CD$_3$OD): δ 1.75 (s, 3 H), 2.44 (s, 1 H), 2.75-2.89 (m, 1 H), 3.02-3.17 (m, 2 H), 3.50-3.64 (m, 3 H), 3.78 (s, 2 H), 4.37-4.80 (m, 1 H), 7.23-7.42 (m, 6 H), 7.72 (d, J=7.98 Hz, 1 H), 7.93 (d, J=7.67 Hz, 1 H).

EXAMPLE 21

2-[3-methyl-1-(1-methyl-3-phenylpropyl)pyrrolidin-
3-yl]-1H-benzimidazole-4-carboxamide The title compound was prepared according to the procedure for Example 11 substituting 4-phenylbutan-2-one for propionaldehyde. MS (APCI) m/z 377 (M+H)$^+$; $^1$H NMR (400 MHz, CD$_3$OD): δ 1.50 (d, J=6.44 Hz, 3 H), 1.72 (d, J=2.76 Hz, 3 H), 1.83-2.00 (m, 1 H), 2.13-2.26 (m, 1 H), 2.27-2.45 (m, 1 H), 2.60-2.71 (m, 1 H), 2.73-2.91 (m, 2 H), 3.35-3.48 (m, 2 H), 3.49-3.86 (m, 2 H), 4.16-4.56 (m, 1 H), 7.15-7.33 (m, 5 H), 7.36 (t, J=7.83 Hz, 1 H), 7.72 (d, J=7.98 Hz, 1 H), 7.92 (d, J=7.06 Hz, 1 H).

EXAMPLE 22

2-(2-methylazetidin-2-yl)-1H-benzimidazole4-car-
boxamide

EXAMPLE 22A dibenzyl azetidine-1,2-dicarboxylate

A suspension of benzyl azetidine-2-carboxylate (4.0 g, 21 mmol) and potassium carbonate (5 g, 36 mmol) in a mixture of 1,4-dioxane (25 ml) and water (30 ml) was treated with benzyl chloroformate (3 ml, 21 mmol) at room temperature for 6 hours. Piperazine (5 drops) was added and the mixture was stirred for additional 0.5 hour. The organic volatiles were removed in vacuo and the residue was partitioned between ethyl acetate and 2 N HCl solution. The organic layer was washed with brine and dried over MgSO$_4$. Removal of solvents gave Example 22A (6.8 g, Yield: 96%). MS (DCI/NH$_3$) m/z 278 (M+H)$^+$.

EXAMPLE 22B dibenzyl 2-methylazetidine-1,2-dicarboxylate

A solution of Example 22A (325 mg, 1 mmol) and iodomethane (0.12 ml, 2.0 mmol) in THF (5 mL) was treated with NaN(TMS)$_2$ in THF (1.0 M, 2 mL, 2.0 mmol) at −70° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and con-

EXAMPLE 22C

1-[(benzyloxy)carbonyl]-2-methylazetidine-2-carboxylic acid

A solution of Example 22B (339 mg, 1.0 mmol) in a mixture of THF (5 mL) and water (3 mL) was treated with LiOH.H$_2$O (84 mg, 2.0 mmol) in water (3 mL). Methanol was added until a transparent solution formed (1 mL). This solution was heated at 60° C. overnight and the organic solvents were removed under vacuum. The residual aqueous solution was acidified with 2 N HCl to pH 2 and was partitioned between ethyl acetate and water. The organic phase was washed with water, dried (MgSO$_4$), filtered and concentrated to give Example 22C (310 mg, 88% yield). MS (DCI/NH$_3$) m/z 250 (M+H)$^+$.

EXAMPLE 22D benzyl 2-({[2-amino-3-(aminocarbonyl)phenyl]amino}carbonyl)-2-methylazetidine-1-carboxylate A solution of Example 22C (1.67 g, 6.55 mmol) in a mixture of pyridine (15 mL) and DMF (15 mL) was treated with 1,1'-carbonyldiimidazole (1.27 g, 7.86 mmol) at 45° C. for 2 h. 2,3-Diamino-benzamide dihydrochloride (1.47 g, 6.55 mmol) was added and the mixture was stirred at rt overnight. After concentration under vacuum, the residue was partitioned between ethyl acetate and diluted sodium bicarbonate aqueous solution. The solid material was collected by filtration, washed with water and ethyl acetate, and dried to give Example 22D (1.88 g). Yield: 75%. MS (APCI) m/z 383 (M+H)$^+$.

EXAMPLE 22E benzyl 2-[4-(aminocarbonyl)-1H-benzimidazol-2-yl]-2-methylazetidine-1-carboxylate A suspension of Example 22D (1.88 g, 4.9 mmol) in acetic acid (50 mL) was heated under reflux for 2 h. After cooling, the solution was concentrated and the residual oil was partitioned between ethyl acetate and sodium bicarbonate aqueous solution. The organic phase was washed with water and concentrated. The residue was purified by flash column chromatography to provide Example 22E (350 mg, Yield: 22%). MS (APCI) m/z 365 (M+H)$^+$.

EXAMPLE 22F 2-(2-methylazetidin-2-yl)-1H-benzimidazole-4-carboxamide

A solution of Example 22E (0.35 g, 1.0 mmol) in methanol (5 ml) was treated with 10% Pd/C (8 mg) under hydrogen overnight. The mixture was filtered and the filtrate was concentrated to provide a solid which was recrystallized from methanol to give 0.21 g of Example 22F. Yield: 93%. MS (APCI) m/z 231 (M+H)$^+$; $^1$H NMR (400 MHz, CD$_3$OD): δ 1.81 (s, 3 H), 2.36-2.44 (m, 2 H), 2.88-2.99 (m, 1 H), 3.00-3.12 (m, 1 H), 7.40 (t, J=7.67 Hz, 1 H), 7.77 (d, J=8.29 Hz, 1 H), 7.95 (d, J=7.67 Hz, 1 H).

EXAMPLE 23

2-(1-isopropyl-2-methylazetidin-2-yl)-1H-benzimidazole-4-carboxamide

The title compound was prepared according to the procedure for Example 11 substituting Example 22F for Example 10E and acetone for propionaldehyde. MS (APCI) m/z 305 (M+H)$^+$; $^1$H NMR (500 MHz, CD$_3$OD): δ 1.30 (d, J=6.55, 6 H), 1.81 (s, 3 H), 2.30-2.56 (m, 2 H), 2.92-3.06 (m, 1 H), 3.08-3.23 (m, 1 H), 3.33-3.50 (m, 1 H), 7.40 (t, J=7.80 Hz, 1 H), 7.77 (d, J=8.11 Hz, 1 H), 7.94 (d, 1 H).

EXAMPLE 24

2-(1-cyclobutyl-2-methylazetidin-2-yl)-1H-benzimidazole-4-carboxamide

The title compound was prepared according to the procedure for Example 11 substituting Example 22F for Example 10E and cyclobutanone for propionaldehyde. MS (APCI) m/z 317 (M+H)$^+$; $^1$H NMR (500 MHz, CD$_3$OD): δ 1.79 (s, 3 H), 1.84-1.95 (m, 2 H), 2.09-2.21 (m, 2 H), 2.24-2.34 (m, 2 H), 2.35-2.46 (m, 2 H), 2.82-2.92 (m, 1 H), 2.99-3.08 (m, 1 H), 3.70-3.80 (m, 1 H), 7.40 (t, 1 H), 7.76 (d, J=6.86 Hz, 1 H), 7.94 (d, J=7.49 Hz, 1 H).

EXAMPLE 25

2-(1-cyclopentyl-2-methylazetidin-2-yl)-1H-benzimidazole-4-carboxamide

The title compound was prepared according to the procedure for Example 11 substituting Example 22F for Example 10E and cyclopentanone for propionaldehyde. MS (DCI) m/z 299 (M+H)$^+$; $^1$H NMR (500 MHz, CD$_3$OD): δ 1.57-1.69 (m, 3 H), 1.75-1.82 (m, 2 H), 1.81 (s, 3 H), 2.03-2.12 (m, 2 H), 2.41-2.49 (m, 2 H), 2.95-3.01 (m, 1 H), 3.13-3.19 (m, 1 H), 3.30-3.32 (m, 1 H), 3.51-3.58 (m, 1 H), 7.42 (t, J=7.96 Hz, 1 H), 7.78 (d, J=8.11 Hz, 1 H), 7.95 (d, J=7.80 Hz, 1 H).

EXAMPLE 26

2-(1-cyclohexyl-2-methylazetidin-2-yl)-1H-benzimidazole-4-carboxamide

The title compound was prepared according to the procedure for Example 11 substituting Example 22F for Example 10E and cyclohexanone for propionaldehyde. MS (APCI) m/z 345 (M+H)$^+$; $^1$H NMR (500 MHz, CD$_3$OD): δ 1.14-1.25 (m, 1 H), 1.26-1.39 (m, 4 H), 1.69 (d, J=12.79 Hz, 1 H), 1.81 (s, 3 H), 1.82-1.90 (m, 2 H), 2.05 (s, 2 H), 2.34-2.50 (m, 2 H), 2.94-3.09 (m, 2 H), 3.11-3.23 (m, 1 H), 7.41 (t, J=7.80 Hz, 1 H), 7.78 (d, J=8.11 Hz, 1 H), 7.95 (d, J=7.80 Hz, 1 H); Anal. Calcd for C$_{18}$H$_{24}$N$_4$O.2.8 TFA: C, 45.55; H, 4.32; N, 9.24. Found: C, 45.15; H, 4.82; N, 8.87.

EXAMPLE 27

2-(3-methylazetidin-3-yl)-1H-benzimidazole-4-carboxamide

EXAMPLE 27A

1-[(benzyloxy)carbonyl]azetidine-3-carboxylic acid

A suspension of azetidine-3-carboxylic acid (2.5 g, 24.75 mmol) and potassium carbonate (4.0 g) in a mixture of 1,4dioxane (25 ml) and water (50 ml) was treated with benzyl chloroformate (4.0 ml, 27.23 mmol) at room temperature for 6 hours. Piperazine (5 drops) was added and the mixture was stirred for additional 0.5 hour. The organic volatiles were removed and the residue was partitioned between ethyl acetate and 2 N HCl solution. The organic layer was washed with brine, dried over $MgSO_4$ and concentrated to give Example 27A (4.8 g, Yield: 83%). MS ($DCI/NH_3$) m/z 236 $(M+H)^+$.

EXAMPLE 27B 1-benzyl 3-methylazetidine-1,3-dicarboxylate

A solution of Example 27A (4.8 g, 20.3 mmol) in ether (100 ml) was treated with diazomethane (100 ml in ether, 60 mmol) at room temperature for 4 hours. Removal of the volatiles gave Example 27B (4.8 g Yield: 98%). MS ($DCI/NH_3$) m/z 250 $(M+H)^+$.

EXAMPLE 27C 1-benzyl 3-methyl 3-methylazetidine-1,3-dicarboxylate

A solution of Example 27B (250 mg, 1 mmol) and iodomethane (0.12 ml, 2.0 mmol) in THF (5 mL) was treated with $NaN(TMS)_2$ in THF (1.0 M, 2 mL, 2.0 mmol) at −70° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and concentrated. The residue was purified by flash chromatography to give Example 27C (220 mg, 85% yield). MS ($DCI/NH_3$) m/z 264 $(M+H)^+$.

EXAMPLE 27D

1-[(benzyloxy)carbonyl]azetidine-3-carboxylic acid

A solution of Example 27C (2.6 g, 10.0 mmol) in a mixture of THF (20 mL) and water (10 mL) was treated with $LiOH·H_2O$ (830 mg, 20.0 mmol) in water (5 mL). Methanol was added until a transparent solution formed (1 mL). This solution was heated at 60° C. overnight and the organic solvents were removed under vacuum. The residual aqueous solution was acidified with 2 N HCl to pH 2 and was partitioned between ethyl acetate and water. The organic phase was washed with water, dried ($MgSO_4$), filtered and concentrated to give Example 27D (2.3 g, 90% yield). MS ($DCI/NH_3$) m/z 235 $(M+H)^+$.

EXAMPLE 27E benzyl 3-({[2-amino-3-(aminocarbonyl)phenyl]amino}carbonyl)-3-methylazetidine-1-carboxylate A solution of Example 27D (250 mg, 1.0 mmol) in a mixture of pyridine (5 mL) and DMF (5 mL) was treated with 1,1'-carbonyldiimidazole (194 mg, 1.2 mmol) at 45° C. for 2 h. 2,3-Diamino-benzamide dihydrochloride (224 mg, 1.0 mmol) was added and the mixture was stirred at rt overnight. After concentration under vacuum, the residue was partitioned between ethyl acetate and diluted sodium bicarbonate aqueous solution. The formed slightly yellow solid material was collected by filtration, washed with water and ethyl acetate, and dried to give Example 27E (270 mg). Yield: 71%. MS (APCI) m/z 383 $(M+H)^+$.

EXAMPLE 27F benzyl 3-[4-(aminocarbonyl)-1H-benzimidazol-2-yl]-3-methylazetidine-1-carboxylate A suspension of Example 27E (280 mg, 0.73 mmol) in acetic acid (10 mL) was heated under reflux for 2 h. After cooling, the solution was concentrated and the residual oil was partitioned between ethyl acetate and sodium bicarbonate aqueous solution. The organic phase was washed with water and concentrated. The residue was purified by flash column chromatography to provide Example 27F (250 mg, Yield: 96%). MS (APCI) m/z 365 $(M+H)^+$.

EXAMPLE 27G 2-(3-methylazetidin-3-yl)-1H-benzimidazole-4-carboxamide

A solution of Example 27F (0.25 g, 0.7 mmol) in methanol (5 ml) was treated with 10% Pd/C (8 mg) under hydrogen overnight. The mixture was filtered and the filtrate was concentrated to provide a solid which was recrystallized from methanol to give 0.110 g of Example 27G. Yield: 69%. MS (APCI) m/z 231 $(M+H)^+$; $^1H$ NMR (500 MHz, $CD_3OD$): δ 1.91 (br s, 3 H), 4.22 (d, J=11.54 Hz, 2 H), 4.69 (d, J=11.54 Hz, 2 H), 7.39 (t, J=7.80 Hz, 1 H), 7.74 (d, J=8.11 Hz, 1 H), 7.95 (d, J=7.49 Hz, 1 H).

EXAMPLE 28

2-(3-methyl-1-propylazetidin-3-yl)-1H-benzimidazole-4-carboxamide

The title compound was prepared according to the procedure for Example 11 substituting Example 27G for Example 10E. MS (APCI) m/z 273 $(M+H)^+$; $^1H$ NMR (400 MHz, $CD_3OD$): δ 1.02 (t, J=7.52 Hz, 3 H), 1.59-1.73 (m, 2 H), 1.92 (s, 3 H), 3.25-3.31 (m, 2 H), 4.28-4.46 (m, 2 H), 4.63-4.80 (m, 2 H), 7.39 (t, J=7.98 Hz, 1 H), 7.75 (d, J=7.06 Hz, 1 H), 7.95 (d, J=7.67 Hz, 1 H).

EXAMPLE 29

2-[1-(cyclopropylmethyl)-3-methylazetidin-3-yl]-1H-benzimidazole4-carboxamide

The title compound was prepared according to the procedure for Example 11 substituting Example 27G for Example 10E and cycolopropanecarbaldehyde for propionaldehyde. MS (APCI) m/z 285 $(M+H)^+$; $^1H$ NMR (500 MHz, $CD_3OD$): δ 0.40-0.48 (m, 2 H), 0.67-0.76 (m, 2 H), 1.02-1.14 (m, J=7.49 Hz, 1 H), 1.81-2.05 (m, 4 H), 3.24 (d, J=7.18 Hz, 2 H), 4.31-4.49 (m, 2 H), 4.68-4.94 (m, 1 H), 7.39 (t, 1 H), 7.75 (d, J=8.11 Hz, 1 H), 7.95 (d, J=7.49 Hz, 1 H); Anal. Calcd for $C_{16}H_{20}N_4O·1.8$ TFA: C, 49.14; H, 4.56; N, 12.06. Found: C, 48.80; H, 4.75; N, 11.83.

EXAMPLE 30

2-(1-isobutyl-3-methylazetidin-3-yl)-1H-benzimidazole-4-carboxamide

The title compound was prepared according to the procedure for Example 11 substituting Example 27G for Example 10E and 2-methylpropionaldehyde for propionaldehyde. MS (APCI) m/z 287 $(M+H)^+$; $^1H$ NMR (400 MHz, $CD_3OD$): δ 1.03 (d, J=6.75 Hz, 6 H), 1.92 (br s, 3 H), 1.96-2.10 (m, 1 H), 3.23 (d, J=7.36 Hz, 2 H), 4.34-4.52 (m, 2 H), 4.68-4.82 (m, 2 H), 7.39 (t, J=7.98 Hz, 1 H), 7.75 (d, J=7.98 Hz, 1 H), 7.95 (d, J=7.06 Hz, 1 H); Anal. Calcd for $C_{16}H_{22}N_4O$·2.4 TFA: C, 45.03; H, 4.53; N, 10.50. Found: C, 45.52; H, 4.72; N, 10.40.

EXAMPLE 31

2-(1-cyclobutyl-3-methylazetidin-3-yl)-1H-benzimidazole-4-carboxamide

The title compound was prepared according to the procedure for Example 11 substituting Example 27G for Example 10E and cyclobutanone for propionaldehyde. MS (APCI) m/z 285 (M+H)$^+$; $^1$H NMR (500 MHz, CD$_3$OD): δ 1.83-2.01 (m, 4 H), 2.14-2.26 (m, 2 H), 2.28-2.42 (m, 2 H), 4.07-4.14 (m, 2 H), 4.30 (d, J=9.36 Hz, 2 H), 4.59-4.83 (m, 2 H), 7.38 (t, 1 H), 7.74 (d, 1 H), 7.95 (d, J=7.49 Hz, 1 H).

EXAMPLE 32

2-(1-cyclopentyl-3-methylazetidin-3-yl)-1H-benzimidazole-4-carboxamide

The title compound was prepared according to the procedure for Example 11 substituting Example 27G for Example 10E and cyclopentanone for propionaldehyde. MS (APCI) m/z 299 (M+H)$^+$; $^1$H NMR (500 MHz, CD$_3$OD): δ 1.57-1.66 (m, 1 H), 1.67-1.76 (m, 2 H), 1.76-1.85 (m, 2 H), 1.86-2.00 (m, 3 H), 2.05-2.17 (m, 2 H), 3.90-3.97 (m, 1 H), 4.31-4.44 (m, 2 H), 4.63-4.79 (m, 2 H), 7.39 (t, J=7.95 Hz, 1 H), 7.75 (d, J=7.80 Hz, 1 H), 7.95 (d, J=7.80 Hz, 1 H).

EXAMPLE 33

2-(1-cyclohexyl-3-methylazetidin-3-yl)-1H-benzimidazole-4-carboxamide

The title compound was prepared according to the procedure for Example 11 substituting Example 27G for Example 10E and cyclohexanone for propionaldehyde. MS (APCI) m/z 313 (M+H)$^+$; $^1$H NMR (400 MHz, CD$_3$OD): δ 1.22 (t, J=12.43 Hz, 3 H), 1.29-1.44 (m, 2 H), 1.73 (d, J=12.89 Hz, 1 H), 1.88 (br s, 3H), 1.79-2.02 (m, 2 H), 2.09 (d, J=10.74 Hz, 2 H), 3.23-3.34 (m, 1 H), 4.36 (s, 2 H), 4.71-4.84 (m, 2 H), 7.39 (t, J=7.82 Hz, 1 H), 7.75 (d, J=7.98 Hz, 1 H), 7.95 (d, J=7.67 Hz, 1 H); Anal. Calcd for $C_{18}H_{24}N_4O$·2.3 TFA: C, 44.04; H, 4.16; N, 8.56. Found: C, 44.96; H, 4.30; N, 8.56.

EXAMPLE 34

2-(3-methyl-1-tetrahydro-2H-pyran-4-ylazetidin-3-yl)-1H-benzimidazole-4-carboxamide The title compound was prepared according to the procedure for Example 11 substituting Example 27G for Example 10E and tetrahydro-4H-pyran-4-one for propionaldehyde. MS (APCI) m/z 315 (M+H)$^+$; $^1$H NMR (500 MHz, CD$_3$OD): δ 1.46-1.61 (m, 2 H), 1.90 (br s, 3 H), 2.02 (dd, J=11.39, 2.96 Hz, 2 H), 3.42 (t, 2 H), 3.52-3.63 (m, 1 H), 4.06 (dd, J=11.70, 4.52 Hz, 2 H), 4.39 (d, J=10.61 Hz, 2 H), 4.79-4.83 (m, 2 H), 7.39 (t, 1 H), 7.75 (d, J=8.11 Hz, 1 H), 7.95 (d, J=6.55 Hz, 1 H); Anal. Calcd for $C_{17}H_{22}N_4O_2$·2.7 TFA: C, 43.43; H, 3.98; N, 9.21. Found: C, 43.05; H, 4.26; N, 8.98.

EXAMPLE 35

2-{1-[(dimethylamino)sulfonyl]-3-methylazetidin-3-yl}-1H-benzimidazole-4-carboxamide To a suspension of Example 27G (50 mg, 0.23 mmol) in methylene chloride (5 mL) was added dimethylsulfamoyl-chloride (50 μL, 0.46 mmol) and triethylamine (80 μL, 0.46 mmol) at room temperature. The reaction mixture was stirred overnight and the homogeneous solution was concentrated. Flash column chromatography of the residue (2-15% CH$_3$OH in CH$_2$Cl$_2$) afforded Example 35 (42 mg, 54% yield). MS (APCI) m/z 338 (M+H)$^+$; $^1$H NMR (500 MHz, CD$_3$OD): δ 1.89 (s, 3 H), 2.84 (s, 6 H), 4.01 (d, J=7.98 Hz, 2 H), 4.46 (d, J=7.98 Hz, 2 H), 7.50 (t, J=7.83 Hz, 1 H), 7.83 (d, J=7.36 Hz, 1 H), 7.98 (d, J=7.67 Hz, 1 H); Anal. Calcd for $C_{14}H_{19}N_5O_3S$·1.7 TFA: C, 39.46; H, 3.90; N, 13.53. Found: C, 39.79; H, 3.43; N, 14.02.

EXAMPLE 36

2-(2-methylpiperidin-2-yl)-1H-benzimidazole-4-carboxamide

EXAMPLE 36A 1-benzyl 2-methyl piperidine-1,2-dicarboxylate

A solution of 1-[(benzyloxy)carbonyl]piperidine-2-carboxylic acid (5 g) and iodomethane (2.5 mL) in DMF (40 mL) was treated with potassium bicarbonate (3.8 g) and stirred at room temperature for 18 hrs. The reaction mixture was concentrated and the residual oil was partitioned between ethyl acetate and water. The organic phase was concentrated and the residue was purified by flash chromatography (silica gel, ethyl acetate/hexanes) to provide Example 36A (4.88 g, Yield: 93%). MS (DCI/NH$_3$) m/z 278 (M+H)$^+$.

EXAMPLE 36B 1-benzyl 2-methyl 2-methylpiperidine-1,2-dicarboxylate

The title compound was prepared according to the procedure for Example 1A substituting Example 36A for 1-benzyl 2-methyl pyrrolidine-1,2-dicarboxylate. MS (DCI/NH$_3$) m/z 292 (M+H)$^+$.

EXAMPLE 36C

1-[(benzyloxy)carbonyl]-2-methylpiperidine-2-carboxylic acid

The title compound was prepared according to the procedure for Example 1B substituting Example 36B for Example 1A. MS (DCI/NH$_3$) m/z 278 (M+H)$^+$

EXAMPLE 36D benzyl 2-({[2-amino-3-(aminocarbonyl)phenyl]amino}carbonyl)-2-methylpiperidine-1-carboxylate The title compound was prepared according to the procedure for Example 1C substituting Example 36C for Example 1B. MS (DCI/NH$_3$) m/z 411 (M+H)$^+$.

EXAMPLE 36E benzyl 2-[4-(aminocarbonyl)-1H-benzimidazol-2-yl]-2-methylpiperidine-1-carboxylate The title compound was prepared according to the procedure for Example 1D substituting Example 36D for Example 1C. MS (DCI/NH$_3$) m/z 393 (M+H)$^+$

EXAMPLE 36F 2-(2-methylpiperidin-2-yl)-1H-benzimidazole4-carboxamide

The title compound was prepared according to the procedure for Example 1E substituting Example 36E for Example 1D. MS (DCI/NH$_3$) m/z 245 (M+H)$^+$; $^1$H NMR (400 MHz, CD$_3$OD) δ 1.53-1.63 (m, 1H), 1.83 (s, 3H), 1.84-1.90 (m, 2H), 1.91-1.99 (m, 1H), 2.14-2.26 (m, 1H), 2.45 (dd, J=14.88, 7.21 Hz, 1H), 3.37-3.51 (m, 2H), 7.44 (t, J=7.82 Hz, 1H), 7.77 (d, J=7.98 Hz, 1H), 8.01 (d, J=6.75 Hz, 1H).

EXAMPLE 37

2-(2-methyl-1-propylpiperidin-2-yl)-1H-benzimidazole-4-carboxamide

The title compound was prepared according to the procedure for Example 11 substituting Example 36F for Example 10E. MS (DCI/NH$_3$) m/z 301 (M+H)$^+$; $^1$H NMR (400 MHz, CD$_3$OD) δ 0.91 (t, J=7.36 Hz, 3H), 1.79-1.93 (m, 4H), 2.01 (s, 3H), 2.02-2.07 (m, 2H), 2.16_2.25 (m, 2H), 2.83-2.98 (m, 1H), 3.02-3.18 (m, 1H), 3.33-3.49 (m, 1H), 3.73-3.84 (m, 1H), 7.45 (t, J=7.83 Hz, 1H), 7.78 (d, J=8.29 Hz, 1H), 8.03 (d, J=7.67 Hz, 1H).

EXAMPLE 38

2-{1-[(dimethylamino)sulfonyl]-4-methylpiperidin-4-yl}-1H-benzimidazole-4-carboxamide

EXAMPLE 38A 1-benzyl 4-ethyl piperidine-1,4-dicarboxylate

A solution of ethyl piperidine-4-carboxylate (30 g) in 1:1 THF/water (300 mL) was treated with cesium carbonate (74.5 g) and benzyl chloroformate (32.2 mL) and stirred at room temperature for 18 hrs. The reaction mixture was partitioned between ethyl acetate and water and the organics concentrated. The residue was purified by flash chromatography (silica gel, ethylacetate/hexanes) to provide Example 38A (50.87 g, Yield: 92%). MS (DCI/NH$_3$) m/z 292 (M+H)$^+$.

EXAMPLE 38B 1-benzyl 4-ethyl 4-methylpiperidine-1,4-dicarboxylate

The title compound was prepared according to the procedure for Example 1A substituting Example 38A for 1-benzyl 2-methyl pyrrolidine-1,2-dicarboxylate (1.5 g, Yield: 41%). MS (DCI/NH$_3$) m/z 306 (M+H)$^+$.

EXAMPLE 38C

1-[(benzyloxy)carbonyl]-4-methylpiperidine-4-carboxylic acid

The title compound was prepared according to the procedure for Example 1B substituting Example 38B for Example 1A (1.37 g, Yield: 99%). MS (DCI/NH$_3$) m/z 278 (M+H)$^+$

EXAMPLE 38D benzyl 4-({[2-amino-3-(aminocarbonyl)phenyl]amino}carbonyl)-4-methylpiperidine-1-carboxylate The title compound was prepared according to the procedure for Example 1C substituting Example 38C for Example 1B. MS (DCI/NH$_3$) m/z 411 (M+H)$^+$.

EXAMPLE 38E benzyl 4-[4-(aminocarbonyl)-1H-benzimidazol-2-yl]-4-methylpiperidine-1-carboxylate The title compound was prepared according to the procedure for Example 1D, substituting Example 38D for Example 1C (0.9 g, Yield: 88%). MS (DCI/NH$_3$) m/z 393 (M+H)$^+$.

EXAMPLE 38F 2-(4-methylpiperidin-4-yl)-1H-benzimidazole-4-carboxamide

The title compound was prepared according to the procedure for Example 1E substituting Example 38E for Example 1D (0.6 g, 99%). MS (DCI/NH$_3$) m/z 259 (M+H)$^+$

EXAMPLE 38G

2-{1-[(dimethylamino)sulfonyl]-4-methylpiperidin-4-yl}-1H-benzimidazole-4-carboxamide To a solution of Example 38F (75 mg) in methylene chloride (5 mL) was added triethylamine (81 μL) and dimethylsulfamoyl chloride (38 μL) at room temperature. Methanol (1 mL) was added until a transparent solution formed. The solution was then stirred at rt for 16 h. The reaction mixture was concentrated and the residue was purified by HPLC (Zorbax C-8, 0.1% TFA/CH$_3$CN/H$_2$O) to provide the title compound as TFA salt (52 mg, 49%). MS (DCI/NH$_3$) m/z 366 (M+H)$^+$; $^1$H NMR (400 MHz, pyridine-d$_5$) δ 1.44 (s, 3H), 1.84-1.95 (m, 2H), 2.54-2.64 (m, 2H), 2.70-2.78 (m, 6H), 3.33-3.45 (m, 2H), 3.56-3.69 (m, 2H), 7.39 (t, J=7.67 Hz, 1H), 7.64 (d, J=7.67 Hz, 1H), 8.45 (s, 1H), 8.62 (d, J=7.67 Hz, 1H), 10.08 (s, 1H); Anal. Calcd for C$_{16}$H$_{23}$N$_5$O$_3$S•1.3 TFA: C, 43.49; H, 4.77; N, 13.63. Found: C, 43.31; H, 4.95; N, 13.42.

EXAMPLE 39

2-(1-cyclobutyl-4-methylpiperidin-4-yl)-1H-benzimidazole-4-carboxamide

The title compound was prepared according to the procedure for Example 11, substituting Example 38F for Example 10E and cyclobutanone for propionaldehyde (30 mg, Yield: 33%). MS (DCI/NH$_3$) m/z 313 (M+H)$^+$; $^1$H NMR (400 MHz, pyridine-d$_5$) δ 1.47 (s,3 H), 1.49-1.55 (m, 1H), 1.59-1.73 (m, 1H), 1.99 (q, J=8.18 Hz, 2H), 2.38-2.65 (m, 4H), 2.73-2.98 (m, 4H), 3.18-3.41 (m, 3H), 7.41 (t, J=7.82 Hz, 1H), 7.69 (d, J=7.98 Hz, 1H), 8.47 (s, 1H), 8.61 (d, J=7.67 Hz, 1H), 9.89 (s, 1H); Anal. Calcd for C$_{18}$H$_{24}$N$_4$O.2.8 TFA: C, 44.87; H, 4.28; N, 8.87. Found: C, 45.04; H. 4.50; N, 9.01.

EXAMPLE 40

2-(1-isopropyl-4-methylpiperidin-4-yl)-1H-benzimidazole-4-carboxamide

The title compound was prepared according to the procedure for Example 11 substituting Example 38F for Example 10E and acetone for propionaldehyde (43 mg, Yield: 49%). MS (DCI/NH$_3$) m/z 301 (M+H)$^+$; $^1$H NMR (400 MHz, pyridine-d$_5$) δ 1.20 (d, J=6.44 Hz, 6H), 1.51 (s, 3H), 2.48-2.70 (m, 2H), 2.73-2.91 (m, 2H), 3.15-3.32 (m, 2H), 3.33-3.52 (m, 3H), 7.39 (t, J=7.82 Hz, 1H), 7.70 (d, J=7.98 Hz, 1H), 8.48 (s, 1H), 8.59 (d, J=7.67 Hz, 1H), 9.88 (s, 1H).

EXAMPLE 41

2-(4-methyl-1-propylpiperidin-4-yl)-1H-benzimidazole-4-carboxamide

The title compound was prepared according to the procedure for Example 11 substituting Example 38F for Example 10E (46 mg, 53%). MS (DCI/NH$_3$) m/z 301 (M+H)$^+$; $^1$H NMR (400 MHz, pyridine-d$_5$) δ 0.74 (t, J=7.36 Hz, 3H), 1.47 (s, 3H), 1.66-1.84 (m, 2H), 2.39-2.63 (m, 2H), 2.76-2.93 (m, 4H), 3.04-3.26 (m, 2H), 3.41-3.62 (m, 2H), 7.40 (t, J=7.67 Hz, 1H), 7.70 (d, J=7.67 Hz, 1H), 8.47 (s, 1H), 8.60 (d, J=7.06 Hz, 1H), 9.89 (s, 1H).

EXAMPLE 42

2-(4-methylazepan-4-yl)-1H-benzimidazole-4-carboxamide

EXAMPLE 42A 1-tert-butyl 4-ethyl 5-oxoazepane-1,4-dicarboxylate tert-Butyl-4-oxo-1-piperidinecarboxylate (10 g, 50.19 mmol) was dissolved in $Et_2O$ (100 ml) and cooled to −78° C. Ethyl diazoacetate (7.3 ml, 70.26 mmol) and $BF_3$.EtO were sequentially added over 30 min. After stirring at the same temperature for 2 h, the reaction was quenched by careful addition of aqueous potassium bicarbonate, during which the cold bath was removed. After warming up to room temperature, the organic layer was washed with water, dried over $Na_2SO_4$ and concentrated. Purification with flash chromatography provided the titled compound (13 g, Yield: 91%). MS (DCI/$NH_3$) m/z 286 (M+H)$^+$.

EXAMPLE 42B 1-tert-butyl 4-ethyl 5-hydroxyazepane-1,4-dicarboxylate

A solution of Example 42A (7.0 g, 24.56 mmol) in MeOH (60 ml) was treated with $NaBH_4$ (933 mg, 24.56 mmol) in several portions at 0° C. The reaction mixture was stirred for additional 2 h and was concentrated. The residue was purified by flash column chromatography (60% EtOAc in Hexane) to give the desired product (3.2 g, Yield: 46%). MS (DCI/$NH_3$) m/z 288 (M+H)$^+$.

EXAMPLE 42C 1-tert-butyl 4-ethyl 5-[(methylsulfonyl)oxy]azepane-1,4-dicarboxylate A solution of Example 42B (250 mg, 1 mmol) and iodomethane (0.12 ml, 2.0 mmol) in THF (5 mL) was treated with NaN(TMS)$_2$ in THF (1.0 M, 2 mL, 2.0 mmol) at −78° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and concentrated. The residue was purified by flash column chromatography to give Example 42C (220 mg, 85% yield). MS (DCI/$NH_3$) m/z 264 (M+H)$^+$.

EXAMPLE 42D 1-tert-butyl 4-ethyl 2,3,6,7-tetrahydro-1H-azepine-1,4-dicarboxylate A solution of example 42C (0.77 g, 2.1 mmol) in 30 mL of benzene was treated with DBU (0.9 ml ) at 60° C. for 1 hour. After cooling, the reaction mixture was concentrated and the residue was purified by flash column chromatography (30% EtOAc in hexane) to give the title product (540 mg, 95% yield). MS (DCI/$NH_3$) m/z 270 (M+H)$^+$.

EXAMPLE 42E 1-tert-butyl 4-ethyl azepane-1,4-dicarboxylate

A solution of example 42D (0.54 g, 2.0 mmol) in 20 ml of MeOH was treated with 10% Pd/C (50 mg) under hydrogen overnight. Solid material was filtered off and the filtrate was concentrated. The residue was purified by flash column chromatography (20% EtOAc in hexane) to give the title product (310 mg, 55% yield). MS (DCI/$NH_3$) m/z 272 (M+H)$^+$.

EXAMPLE 42F 1-tert-butyl 4-ethyl 4-methylazepane-1,4-dicarboxylate

A solution of Example 42E (1.7 g, 6.27 mmol) and iodomethane (0.8 ml, 12.55 mmol) in THF (15 mL) was treated with LDA (2.0 M solution in THF, 6.3 mL, 12.55 mmol) at −78° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and concentrated. The residue was purified by flash chromatography (20-40% EtOAc in hexane) to give the title product (1.2 g, 67% yield). MS (DCI/$NH_3$) m/z 286 (M+H)$^+$.

EXAMPLE 42G ethyl 4-methylazepane4-carboxylate

A solution of Example 42F (1.4 g, 5.6 mmol) in THF (50 mL) was treated with TFA (2.0 ml) at room temperature overnight. Removal of the volatiles provided Example 42G as TFA salt which was used in the next step without further purification. MS (DCI/$NH_3$) m/z 186 (M+H)$^+$.

EXAMPLE 42H 1-benzyl 4-ethyl 4-methylazepane-1,4-dicarboxylate

A suspension of Example 42G (1.0 g, 5.6 mmol) and potassium carbonate (3.0 g) in a mixture of dioxan (25 ml) and water (50 ml) was treated with benzyl chloroformate (0.82 ml, 5.6 mmol) at room temperature for 6 hours. Piperazine (5 drops) was added and the mixture was stirred for additional 0.5 hour. The organic solvent was removed in vacuo and the residue was partitioned between ethyl acetate and 2 N HCl solution. The organic layer was washed with brine and concentrated to give the desired compound (1.48 g, Yield: 85%). MS (DCI/NH1$_3$) m/z 306 (M+H)$^+$.

EXAMPLE 42I

1-[(benzyloxy)carbonyl]-4-methylazepane-4-carboxylic acid

A solution of Example 42H (1.6 g, 5.0 mmol) in a mixture of THF (20 mL) and water (10 mL) was treated with LiOH.H$_2$O (530 mg, 12.2 mmol) in water (5 mL). Methanol was added until a transparent solution formed (5 mL). This solution was heated at 60° C. for overnight and the organic solvents were removed under vacuum. The residual aqueous solution was acidified with 2 N HCl to pH 2 and was partitioned between ethyl acetate and water. The organic phase was washed with water, dried (MgSO$_4$), filtered and concentrated to give Example 42I (0.9 g, 62% yield). MS (DCI/NH$_3$) m/z 292 (M+H)$^+$.

EXAMPLE 42J benzyl 4-({[2-amino-3-(aminocarbonyl)phenyl]amino}carbonyl)-4-methylazepane-1-carboxylate A solution of Example 42I (291 mg, 1.0 mmol) in a mixture of pyridine (5 mL) and DMF (5 mL) was treated with 1,1'-carbonyldiimidazole (194 mg, 1.2 mmol) at 45° C. for 2 h. 2,3-Diamino-benzamide dihydrochloride (224 mg, 1.0 mmol) was added and the mixture was stirred at rt overnight. After concentration under vacuum, the residue was partitioned between ethyl acetate and diluted sodium bicarbonate aqueous solution. The formed slightly yellow solid material was collected by filtration, washed with water and ethyl acetate, and dried to give Example 42J (288 mg). Yield: 68%. MS (APCI) m/z 425 (M+H)$^+$.

EXAMPLE 42K benzyl 4-[4-(aminocarbonyl)-1H-benzimidazol-2-yl]-4-methylazepane-1-carboxylate A suspension of Example 42J (288 mg, 0.68 mmol) in acetic acid (10 mL) was heated under reflux for 2 h. After cooling, the solution was concentrated and the residue partitioned between ethyl acetate and aqueous sodium bicarbonate solution. The organic phase was washed with water and concentrated. The residue was purified by flash column chromatography to provide Example 42K (233 mg, Yield: 80%). MS (APCI) m/z 407 (M+H)$^+$.

EXAMPLE 42L 2-(4-methylazepan4-yl)-1H-benzimidazole-4-carboxamide

A solution of Example 42K (70 mg, 0.17 mmol) in methanol (5 ml) was treated with 10% Pd/C (8 mg) under hydrogen overnight. The mixture was filtered and the filtrate was concentrated. The residue was purified by HPLC (Zorbax C-18, 0.1 TFA/CH$_3$CN/H$_2$O) to give the desired product (55 mg, 57% yield). MS (APCI) m/z 273 (M+H)$^+$. $^1$H NMR (500 MHz, CD$_3$OD): δ 1.56 (s, 3 H), 1.88-1.97 (m, 1 H), 1.97-2.05 (m, 1 H), 2.05-2.13 (m, 1 H), 2.16-2.26 (m, 1 H), 2.57 (dd, J=14.97, 8.11 Hz, 1 H), 2.82 (dd, J=16.22, 6.86 Hz, 1 H), 3.22-3.29 (m, 1 H), 3.29-3.33 (m, 1 H), 3.34-3.49 (m, 2 H), 7.43 (t, J=7.80 Hz, 1 H), 7.78 (d, J=8.11 Hz, 1 H), 7.95 (d, J=6.86 Hz, 1 H);
Anal. Calcd for C$_{15}$H$_{20}$N$_4$O.2.8 TFA: C, 42.41; H, 3.91; N, 9.89. Found: C, 41.90; H, 4.09; N, 9.41.

EXAMPLE 43

2-(1-cyclopentyl-4-methylazepan-4-yl)-1H-benzimidazole-4-carboxamide

The title compound was prepared according to the procedure for Example 11, substituting Example 42L for Example 10 E and cyclopantanone for propionaldehyde. MS (APCI) m/z 341 (M+H)$^+$; $^1$H NMR (500 MHz, CD$_3$OD): δ 1.50-1.53 (m, 3 H), 1.54-1.60 (m, 3 H), 1.62-1.78 (m, 4 H), 1.85 (s, 2 H), 1.90-2.07 (m, 3 H), 2.07-2.28 (m, 3 H), 2.30-2.67 (m, 1 H), 2.69-3.02 (m, 1 H), 3.11-3.28 (m, 1 H), 3.35-3.49 (m, 1 H), 3.50-3.79 (m, 2 H), 7.40 (t, 1 H), 7.74 (d, 1 H), 7.94 (d, J=6.86 Hz, 1 H).

EXAMPLE 44

2-(1-Cyclohexyl-4-methyl-azepane-4-yl)-H-benzoimidazole-4-carboxylic acid amide

The title compound was prepared according to the procedure for Example 11, substituting Example 42L for Example 10 E and cyclohexanone for propionaldehyde. MS (APCI) m/z 355 (M+H)$^+$; $^1$H NMR (500 MHz, CD$_3$OD): δ 1.15-1.77 (m, 8 H), 1.55 (s, 3H), 1.87-2.22 (m, 8H), 2.30-2.82 (m, 1H), 2.46-2.96 (m, 1H), 3.22-3.50 (m, 2H), 3.38-3.60 (m, 1H), 7.39 (t, 1H), 7.75 (d, J=8.11 Hz, 1H), 7.94 (d, J=7.49 Hz, 1H).

EXAMPLE 45

2-[1-(2-fluorobenzyl)-3-methylpyrrolidin-3-yl]-1H-benzimidazole-4-carboxamide

A solution of Example 10 (50 mg, 0.18 mmol) in methanol (10 mL) was treated with 2-fluorobenzaldehyde (45 mg, 0.36 mmol) at rt overnight. Sodium triacetoxyborohydride (84 mg, 0.40 mmol) was then added and the solution was stirred at it for 3 h. After concentration, the residue was separated by HPLC (Zorbax C-18, 0.1% TFA/CH$_3$CN/H$_2$O) to provide the title compound as TFA salt (26 mg). MS (DCI) m/z 353 (M+H)$^+$; $^1$H NMR (500 MHz, CD$_3$OD): δ 1.74 (s, 3 H); 2.43 (m, 1 H), 2.82 (m, 1 H); 3.62 (m, 2 H); 3.70 (m, 1 H); 4.44 (d, J=12.21 Hz, 1 H); 4.62 (s, 2 H); 7.36 (m, 3 H); 7.52 (m, 1 H); 7.63 (m, 1 H); 7.71 (d, J=7.32 Hz, 1 H); 7.92 (d, J=7.63 Hz, 1 H).

EXAMPLE 46

6-chloro-2-(3-methylpyrrolidin-3-yl)-1H-benzimidazole-4-carboxamide

EXAMPLE 46A

2-Amino-5-chloro-3-nitro-benzamide

A solution of 2-amino-3-nitro-benzamide (4.0 g, 22.08 mmol), which was synthesized as described in previous patent application WO0026192, in anhydrous acetonitrile (1250 mL) was treated with N-chlorosuccinimide (3.1 g, 23.18 mmol) at 60° C. for overnight. After cooling to room temperature, the formed orange crystalline material was collected by filtration, washed with acetonitrile and dried to give 2.95 g of Example 46A. The mother liquor was concentrated and the residue was recrystallized in acetonitrile (300 mL). The formed orange crystalline material was collected by filtration, washed with acetonitrile, and dried to provide Example 46A (800 mg, total yield: 79%). MS (DCI/NH$_3$) m/z 216 (M+H)$^+$.

EXAMPLE 46B 2,3-Diamino-5-chloro-benzamide dihydrochloride

A solution of Example 46A (650 mg, 3.0 mmol) in a mixture of THF (100 mL) and ethanol (100 mL) was treated with Raney nickel (50% in water, 300 mg) under hydrogen at room temperature for 3 hours. Solid material was filtered off The filtrate was treated with HCl in ether (1.0 M, 6 mL) and concentrated to give Example 46B (780 mg, 100%). MS (DCI/NH$_3$) m/z 186 (M+H)$^+$.

EXAMPLE 46C 6-chloro-2-(3-methylpyrrolidin-3-yl)-1H-benzimidazole4-carboxamide A solution of Example 10B (500 mg, 1.9 mmol) in methylene chloride (10 ml) was treated with oxalyl chloride (0.17 ml, 1.9 mmol) and 2 drops of DMF at rt for 1 hour. The volatiles were removed and the residue was dissolved in methylene chloride (20 ml). This acyl chloride solution was then added into a solution of Example 46B (353 mg, 1.9 mmol) and triethylamine (1 ml) in THF (10 mL). The reaction mixture was stirred at rt overnight and concentrated. The residue was treated with 10 ml of acetic acid at 80° C. overnight. After concentration, the residue was separated by flash chromatography (silica gel, EtOAc) to give Example 46C (690 mg, 88%).

EXAMPLE 46D 6-chloro-2-(3-methylpyrrolidin-3-yl)-1H-benzimidazole-4-carboxamide A solution of Example 46C (690 mg) in 20 ml of TFA was heated under reflux for 6 hours. After cooling, the volatiles were removed and the residue was purified by HPLC (Zorbax C-18, 0.1% TFA/CH$_3$CN/H$_2$O) to provide Example 46D as TFA salt (340 mg). The HCl salt was prepared by dissolving the TFA salt in a mixture of methylene chloride and methanol and treating with 1M HCl solution in ether. Removal of the volatiles provided the title compound as HCl salt. MS (DCI) m/z 279 (M+H)$^+$; $^1$H NMR (400 MHz, CD$_3$OD): δ 1.72 (s, 3 H); 2.35 (m, 1 H); 2.73 (m, 1 H); 3.35 (d, J=11.66 Hz, 1 H); 3.48 (m, 1 H); 3.61 (m, 1 H); 4.21 (d, J=11.66 Hz, 1 H); 7.66 (d, J=2.15 Hz, 1 H); 7.80 (d, J=1.84 Hz, 1 H); Anal. Calcd for C$_{13}$H$_{15}$ClN$_4$O.2.0 TFA: C, 40.29; H, 3.38; N, 11.06. Found: C, 40.72; H, 3.28; N, 11.10.

EXAMPLE 47

6-chloro-2-(1,3-dimethylpyrrolidin-3-yl)-1H-benzimidazole-4-carboxamide

A solution of Example 46D as HCl salt (80 mg, 0.22 mmol) in methanol (5 mL) was treated with triethylamine (92 μL, 0.66 mmol) and formaldehyde (37 wt % in water, 80 μL, 1.08 mmol) at room temperature for 1 hour. Sodium cyanoborohydride (67 mg, 1.08 mmol) was then added and the solution was heated at 50° C. for 5 hours. After cooling, the reaction mixture was concentrated and the residue was separated by HPLC (Zorbax, C-18, 250×2.54 column, Mobile phase A: 0.1% TFA in H$_2$O; B: 0.1% TFA in CH$_3$CN; 0-100% gradient) to provide Example 47 as TFA salt. This material was dissolved in 3 mL of 1:1 mixture of methylene chloride and methanol and treated with HCl in ether (1.0 M, 10 mL). Removal of the volatiles afforded Example 47 as HCl salt (70 mg, 83%). MS (APCI) m/z 293 (M+H)$^+$; $^1$H NMR (500 MHz, CD$_3$OD): δ 1.82 (s, 3 H), 2.50 (m, 0.5 H), 2.60 (m, 0.5 H), 2.83-2.98 (m, 1.5 H), 3.07 (s, 1.5 H), 3.31 (s, 1.5 H), 3.40-3.52 (m, 2 H), 3.85-4.10 (m, 2 H), 4.51 (d, J=12.21 Hz, 0.5 H), 7.88 (s, 0.5 H), 7.92 (s, 0.5 H), 7.99 (s, 0.5 H), 8.03 (s, 0.5 H); Anal. Calcd for C$_{14}$H$_{17}$ClN$_4$O.2.5 HCl: C, 43.80; H, 5.12; N, 14.59. Found: C, 43.73; H, 5.44; N, 14.27.

EXAMPLE 48

6-chloro-2-(1-isopropyl-3-methylpyrrolidin-3-yl)-1H-benzimidazole4-carboxamide

The title compound as TFA salt was prepared according to the procedure for Example 47, substituting acetone for formaldehyde. Yield: 50%. MS (APCI) m/z 321 (M+H)$^+$; $^1$H NMR (500 MHz, CD$_3$OD): δ 1.38-1.47 (m, 6 H), 1.73 (s, 3 H), 2.26-2.33 (m, 0.5 H), 2.38-2.43 (m, 0.5 H), 2.73-2.84 (m, 1 H), 3.34-3.40 (m, 1 H), 3.52-3.62 (m,2 H), 3.71-3.82 (m, 2 H), 4.25 (d, J=12.21 Hz, 0.5 H), 4.47 (d, J=11.60 Hz, 0.5 H), 7.70 (s, 1 H), 7.86 (s, 0.5 H), 7.88 (s, 0.5 H); Anal. Calcd for C$_{16}$H$_{21}$ClN$_4$O.2.15 TFA: C, 43.08; H, 4.12; N, 9.90. Found: C, 43.04; H, 4.13, N, 9.82.

EXAMPLE 49

2-(2-methylpyrrolidin-2-yl)-6-(trifluoromethyl)-1H-benzimidazole-4-carboxamide

EXAMPLE 49A 2-(4-Bromo-6-trifluoromethyl-1H-benzoimidazol-2-yl)-2-methyl-pyrrolidine-1-carboxylic acid benzyl ester A solution of Example 1B (1.0 g, 3.8 mmol) in a mixture of pyridine (15 mL) and DMF (15 mL) was treated with 1,1'-carbonyldiimidazole (739 mg, 4.6 mmol) at 40° C. for 30 minutes. 2,3-Diamino-1-bromo-5-trifluoromethylbenzene (969 mg, 3.8 mmol) was added and the mixture was stirred at rt overnight. After concentration under vacuum, the residue was suspended in 20 ml of acetic acid. This mixture was heated at 80° C. overnight. After cooling, the acetic acid was removed by rotavapor and the residue was separated by flash chromatography (silica gel, EtOAc) to give Example 49A (500 mg, 30%). MS (DCI/NH$_3$) m/z 483 (M+H)$^+$.

EXAMPLE 49B 2-(4-Cyano-6-trifluoromethyl-1H-benzoimidazol-2-yl)-2-methyl-pyrrolidine-1-carboxylic acid benzyl ester A suspension of Example 49A (482 mg, 1.0 mmol), zinc cyanide (293 mg, 1.2 mmol) and tetrakis(triphenylphosphine)palladium (0) (231 mg, 0.2 mmol) in anhydrous DMF (15 ml) was heated under nitrogen at 90° C. overnight. After cooling, the reaction mixture was partitioned between ethyl acetate and brine. The organic phase was washed with brine, water and concentrated. The residue was separated by flash chromatography (silica gel, Ethyl acetate) to provide Example 49B (320 mg, 75%). MS (DCI/NH$_3$) m/z 429 (M+H)$^+$.

EXAMPLE 49C 2-(2-methylpyrrolidin-2-yl)-6-(trifluoromethyl)-1H-benzimidazole-4-carboxamide A solution of Example 49B (50 mg, 0.12 mmol) in 38% HBr in acetic acid (10 ml) was aged at room temperature overnight. The volatiles were removed and the residue was separated by HPLC (Zorbax, C-18, 250×2.54 column, Mobile phase A: 0.1% TFA in H$_2$O; B: 0.1% TFA in CH$_3$CN; 0-100% gradient) to provide Example 49C as TFA salt (24 mg). MS (DCI): m/z 313 (M+H)+; ¹H NMR (400 MHz, CD₃OD): δ 1.97 (s, 3 H); 2.12 (m, 1 H); 2.33 (m, 1 H); 2.43 (m, 1 H); 2.63 (m, 1 H); 3.65 (m, 2 H); 8.06 (s, 1 H); 8.24 (s, 1 H); Anal. Calcd for $C_{14}H_{15}F_3N_4O \cdot 1.8$ TFA: C, 40.85; H, 3.27; N, 10.83. Found: C, 40.76; H, 3.33; N, 10.99.

EXAMPLE 50

2-(1,2-dimethylpyrrolidin-2-yl)-6-(trifluoromethyl)-1H-benzimidazole-4-carboxamide The title compound as TFA salt was prepared according to the procedure for Example 47, substituting Example 49C for Example 46D. MS (DCI) m/z 327 (M+H)+; ¹H NMR (500 MHz, CD₃OD) δ 1.97(s, 3 H); 2.36 (m, 2 H); 2.58 (m, 2 H) 2.99 (s, 3 H); 3.58 (m, 1 H); 3.90 (m, 1 H); 8.08 (s, 1 H); 8.25 (s, 1 H); Anal. Calcd for $C_{15}H_{17}F_3N_4O \cdot 1.8$ TFA: C, 42.03; H, 3.56; N, 10.54. Found: C, 41.87; H, 3.44; N, 10.54.

EXAMPLE 51

6-fluoro-2-(2-methylpyrrolidin-2-yl)-1H-benzimidazole-4-carboxamide

EXAMPLE 51A

2-Bromo-4-fluoro-6-nitro-phenylamine

To a solution of 4-fluoro-2-nitroaniline (40.0 g, 0.256 mol) in a mixture of dichloromethane (900 mL) and acetic acid (300 mL) was added bromine (39.4 mL, 0.768 mol) at 0° C. The reaction mixture was stirred at this temperature for 1 h and at room temperature for 18 h. After concentration, the residue was partitioned between ethyl acetate and aqueous sodium bicarbonate solution. The organic phase was washed with sodium bisulphite solution (300 ml), water and concentrated. The residual solid was recrystallized from hexanes/dichloromethane (10:1) to provide Example 51A (48 g, 79%). MS (DCI/NH₃) m/z 236 (M+H)+.

EXAMPLE 51B

2-Amino-5-fluoro-3-nitro-benzonitrile

A suspension of Example 51A (35.0 g, 0.15 mol), zinc cyanide (34.98 g, 0.3 mol) and tetrakis(triphenylphosphine) palladium (0) (12.05 g, 10 mmol) in anhydrous DMF (420 mL) was heated under nitrogen at 95° C. for 22 h. After cooling, insoluble material was filtered off and the filtrate was partitioned between ethyl acetate and brine. The organic phase was washed with water and concentrated. The residual solid was recrystallized from methanol to provide Example 51B (24 g, 89%). MS (DCI/NH₃) m/z 182 (M+H)+.

EXAMPLE 51C 2,3-Diamino-5-fluoro-benzonitrile

A solution of Example 51B (1.4 g, 7.72 mmol) in a mixture of tetrahydrofuran (60 mL) and ethanol (60 mL) was treated with Raney nickel (50% in water, 0.8 g) under hydrogen for 4 hours. The solid material was filtered off and the filtrate was concentrated to provide Example 51C (1.17 g, 100%). MS (DCI/NH₃) m/z 152 (M+H)+.

EXAMPLE 51D 2-(4-Cyano-6-fluoro-1H-benzoimidazol-2-yl)-2-methyl-pyrrolidine-1-carboxylic acid benzyl ester A solution of Example 1B (574 mg, 2.18 mmol) in methylene chloride (8 mL) was treated with oxalyl chloride (285 μL, 3.27 mmol) and one drop of DMF at room temperature for 1 hour. After concentration, the residue was dissolved in methylene chloride (8 mL) and the solution was added to a solution of Example 51C (329 mg, 2.18 mmol) and triethylamine (364 μL, 2.62 mmol) in THF (8 mL). This reaction mixture was stirred at room temperature overnight before it was concentrated. The residue was dissolved in 15 mL of acetic acid and this solution was heated at 100° C. for 1 hour. After cooling, the acetic acid was removed by rotavapor and the residue was partitioned between ethyl acetate and aqueous sodium bicarbonate solution. The organic layer was washed with sodium bicarbonate solution, water and concentrated. The residue was purified by flash chromatography (silica gel, 20-70% gradient EtOAc in hexane) to give Example 51D (679 mg, 82%). MS (DCI/NH₃) m/z 379 (M+H)+.

EXAMPLE 51E 6-fluoro-2-(2-methylpyrrolidin-2-yl)-1H-benzimidazole-4-carboxamide A solution of Example 51D (460 mg, 1.21 mmol) in acetic acid (3 mL) was treated with 30% HBr/acetic acid (6 mL) at room temperature for 2 h. Water was added and the mixture was extracted with hexanes (2×50 mL). The clear aqueous solution was concentrated and the residue was purified by HPLC (Zorbax, C-18, 250×2.54 column, Mobile phase A: 0.1% TFA in water; B: 0.1% TFA in Acetonitrile, 0-100% gradient) to provide Example 51 as TFA salt. This product was dissolved in a mixture of methylene chloride and methanol and treated with 1M HCl solution in ether. Removal of the volatiles provided Example 51E as HCl salt (327 mg, 75%). MS (DCI/NH₃) m/z 263 (M+H)+; ¹H NMR (400 MHz, CD₃OD): δ 1.98 (s, 3 H), 2.09-2.19 (m, 1 H), 2.29-2.38 (m, 1 H), 2.42-2.48 (m, 1 H), 2.55-2.64 (m, 1 H), 3.61-3.74 (m, 2 H), 7.33 (dd, J=8.24, 2.44 Hz, 1H), 7.37 (dd, J=8.24, 2.45 Hz, 1 H); Anal. Calcd for $C_{13}H_{15}FN_4O \cdot 2.6$ HCl: C, 43.73; H, 4.97; N, 15.69. Found: C, 43.68; H, 5.30; N, 15.81.

EXAMPLE 52

6-chloro-2-(2-methylpyrrolidin-2-yl)-1H-benzimidazole-4-carboxamide

The title compound as HCl salt was prepared according to the procedures for Examples 46C and 46D, substituting Example 1 B for Example 10B used in Example 46C. MS (APCI/NH₃) m/z 277 (M+H)⁻; ¹H NMR (500 MHz, CD₃OD): δ 1.94 (s, 3 H), 2.05-2.13 (m, 1 H), 2.26-2.34 (m, 1 H), 2.36-2.43 (m, 1 H), 2.54-2.60 (m, 1 H), 3.55-3.62 (m, 1 H), 3.62-3.69 (m, 1 H), 7.77 (d, J=1.83 Hz, 1 H), 7.94 (d, J=2.14 Hz, 1 H), Anal. Calcd for $C_{13}H_{15}ClN_4O.2.55$ HCl: C, 42.21; H, 4.77; N, 15.15. Found: C, 42.65; H, 5.48; N, 14.51.

EXAMPLE 53

6-chloro-2-[(2R)-2-methylpyrrolidin-2-yl]-1H-benzimidazole-4-carboxamide

The title compound as TFA salt was prepared according to the procedures for Examples 46C and 46D, substituting (R)-2-methyl-pyrrolidine-1,2-dicarboxylic acid 1-benzyl ester (prepared according to the procedure as described in Overberger, C. G.; Jon, Y. S. J. Polymer Science 1977, 15, 1413-1421) for Example 10B used in Example 46C. MS (DCI) m/z 279 (M+H)$^+$; $^1$H NMR (400 MHz, CD$_3$OD): δ 1.95 (s, 3 H); 2.10 (m, 1 H); 2.28 (m, 1 H); 2.40 (m, 1 H); 2.60 (m, 1 H); 3.65 (m, 2 H); 7.73 (s, 1 H); 7.88 (s, 1 H); Anal. Calcd for $C_{13}H_{15}ClN_4O.1.5$ TFA: C, 42.73; H, 3.59; N, 12.45. Found: C, 42.94; H. 3.69; N, 12.60.

EXAMPLE 54

6-chloro-2-[(2S)-2-methylpyrrolidin-2-yl]-1H-benzimidazole-4-carboxamide

The title compound as TFA salt was prepared according to the procedures for Examples 46C and 46D, substituting (S)-2-methyl-pyrrolidine-1,2-dicarboxylic acid 1-benzyl ester (prepared according to the procedure as described in Overberger, C. G.; Jon, Y. S. J. Polymer Science 1977, 15, 1413-1421) for Example 10B used in Example 46C. MS (DCI) m/z 279 (M+H)$^+$; $^1$H NMR (500 MHz, CD$_3$OD): δ 1.94 (s, 3 H); 2.10 (m, 1 H); 2.30 (m, 1 H); 2.42 (m, 1 H); 2.58 (m, 1 H); 3.65 (m, 2 H); 7.75 (s, 1 H); 7.90 (s, 1 H); Anal. Calcd for $C_{13}H_{15}ClN_4O.1.6$ TFA: C, 43.70; H, 3.67; N, 12.78. Found: C, 43.82; H, 3.78; N, 12.98.

EXAMPLE 55

6-fluoro-2-[(2S)-2-methylpyrrolidin-2-yl]-1H-benzimidazole4-carboxamide

The title compound as TFA salt was prepared according to the procedures for Examples 51D and 51E, substituting (S)-2-methyl-pyrrolidine-1,2-dicarboxylic acid 1-benzyl ester (prepared according to the procedure as described in Overberger, C. G.; Jon, Y. S. J. Polymer Science 1977, 15, 1413-1421) for Example 1B used in Example 51D. MS (DCI/NH$_3$) m/z 263 (M+H)$^+$; $^1$H NMR (400 MHz, CD$_3$OD): δ 1.93 (s, 3 H), 2.03-2.15 (m, 1 H), 2.25-2.32 (m, 1 H), 2.35-2.42 (m, 1 H), 2.53-2.62 (m, 1 H), 3.54-3.60 (m, 1 H), 3.62-3.69 (m, 1 H), 7.49 (dd, J=8.29, 2.46 Hz, 1 H), 7.72 (dd, J=10.59, 2.30 Hz, 1 H); Anal. Calcd for $C_{13}H_{15}FN_4O.1.5$ TFA: C, 44.35; H, 3.72; N, 12.92. Found: C, 44.93; H, 3.78; N, 13.21.

EXAMPLE 56

6-fluoro-2-[(2R)-2-methylpyrrolidin-2-yl]-1H-benzimidazole-4-carboxamide

EXAMPLE 56A (R)-2-Methyl-pyrrolidine-1,2-dicarboxylic acid 1-benzyl ester

A solution of Example 74D (20 g) in dichloromethane (150 mL) was treated with TFA (80 mL) at 0° C. The ice-bath was removed and the mixture was stirred at ambient temperature for 3 h. Acetonitrile was added and the reaction mixture was concentrated. The residue was dissolved in a mixture of tetrahydrofuran (150 mL) and water (150 mL). Cs$_2$CO$_3$ (170.5 g) and benzyl chloroformate (14.7 mL) was then added. The reaction mixture was stirred at ambient temperature for 16 hours and was concentrated. The residue was diluted with 0.5 N NaOH solution, and was extracted with 20% Ether in hexanes. The aqueous layer was acidified with 2N HCl solution to a pH 3 and the mixture was extracted with ethyl acetate. The combined organic phases were concentrated and the residue purified by flash chromatography (silica gel, 5%-90% gradient EtOAc in hexanes) to provide the title compound (22.7 g, 99%). MS (DCI/NH$_3$) m/z 264 (M+H)$^+$.

EXAMPLE 56B 6-fluoro-2-[(2R)-2-methylpyrrolidin-2-yl]-1H-benzimidazole4-carboxamide The title compound as HCl salt was prepared according to the procedures for Examples 51D and 51E, substituting Example 56A for Example 1B used in Example 51D. MS (DCI/NH$_3$) m/z 263 (M+H)$^+$; $^1$H NMR (500 MHz, CD$_3$OD): δ 1.96 (s, 3H), 2.05-2.14 (m, 1H), 2.26-2.36 (m, 1H), 2.38-2.47 (m, 1H), 2.56-2.65 (m, 1H), 3.57-3.63 (m, 1H), 3.64-3.70 (m, 1H), 7.52 (dd, J=8.24, 2.44 Hz, 1H), 7.72 (dd, J=10.37, 2.44 Hz, 1H); Anal. Calcd for $C_{13}H_{15}FN_4O.2.5$ HCl.0.25 H$_2$O: C, 43.62; H, 5.07; N, 15.65. Found: C, 43.85; H, 5.47; N, 15.43.

EXAMPLE 57

6-chloro-2-[(2R)-1,2-dimethylpyrrolidin-2-yl]-1H-benzimidazole-4-carboxamide

The title compound as TFA salt was prepared according to the procedure for Example 47, substituting Example 53 for Example 46D. MS (DCI) m/z 293 (M+H)$^+$; $^1$H NMR (500 MHz, CD$_3$OD): δ 1.93 (s, 3 H); 2.23 (m, 1 H); 2.33 (m, 1 H); 2.54 (m, 2 H); 3.00 (s, 3 H); 3.54 (m, 1 H); 3.98 (m, 1 H); 7.77 (s, 1 H); 7.93 (s, 1 H); Anal. Calcd for $C_{14}H_{17}ClN_4O.1.4$ TFA: C, 44.56; H, 4.10; N. 12.38. Found: C, 44.46; H, 4.20; N, 12.59

EXAMPLE 58

6-chloro-2-[(2R)-1-isopropyl-2-methylpyrrolidin-2-yl]-1H-benzimidazole-4-carboxamide The title compound as TFA salt was prepared according to the procedure for Example 47, substituting Example 53 for Example 46D and acetone for formaldehyde. MS (DCI) m/z 321 (M+H)$^+$; $^1$H NMR (500 MHz, CD$_3$OD): δ 1.09 (br s, 3 H); 1.45 (br s, 3 H); 2.02 (s, 3 H); 2.36 (m, 2 H); 2.54 (m, 2 H); 3.62 (m, 1 H); 3.81 (m, 1 H); 3.98 (m, I H); 7.77 (s, 1 H); 7.93 (s, 1 H), Anal. Calcd for $C_{16}H_{21}ClN_4O.1.7$ TFA: C, 45.23; H, 4.41; N, 10.88. Found: C, 45.55; H, 4.32; N, 11.00

EXAMPLE 59

6-chloro-2-[(2R)-1-cyclopentyl-2-methylpyrrolidin-2-yl]-1H-benzimidazole4-carboxamide The title compound as TFA salt was prepared according to the procedure for Example 47, substituting Example 53 for Example 46D and cyclopentanone for formaldehyde. MS (DCI) m/z 347 (M+H)$^+$; $^1$H NMR (500 MHz, CD$_3$OD): δ 1.12 (m, 1 H); 1.59 (m,3 H); 1.75 (m, 1 H); 1.77 (m, 1 H); 2.03 (s, 3 H); 2.16 (m, 1 H); 2.36 (m, 2 H); 2.49 (m, 2 H); 2.70 (m, 1 H), 3.63 (m, 1 H); 3.81 (m, 1 H); 3.98 (m, 1 H); 7.78 (s, 1 H); 7.94 (s, 1 H); Anal. Calcd for C$_{18}$H$_{23}$ClN$_4$O.1.8 TFA: C, 42.76; H, 3.50; N, 11.87. Found: C, 42.65; H, 3.33; N, 11.78.

EXAMPLE 60

6-chloro-2-[(2S)-1,2-dimethylpyrrolidin-2-yl]-1H-benzimidazole4-carboxamide

The title compound as TFA salt was prepared according to the procedure for Example 47, substituting Example 54 for Example 46D. MS (DCI) m/z 293 (M+H)$^+$; $^1$H NMR (400 MHz, CD$_3$OD): δ 1.95 (s, 3 H); 2.27 (m, 2 H); 2.54 (m, 2 H); 2.99 (s, 3 H); 3.57 (m, 1 H); 3.90 (m, 1 H); 7.75 (d, J=1.84 Hz, 1 H), 7.90 (d, J=1.84 Hz, 1 H); Anal. Calcd for C$_{14}$H$_{17}$ClN$_4$O.1.4 TFA: C, 44.56; H, 4.07; N, 12.38. Found: C, 44.66; H, 4.10; N, 12.66.

EXAMPLE 61

6-chloro-2-[(2S)-1-isopropyl-2-methylpyrrolidin-2-yl]-1H-benzimidazole-4-carboxamide The title compound as TFA salt was prepared according to the procedure for Example 47, substituting Example 54 for Example 46D and acetone for formaldehyde. MS (DCI) m/z 321 (M+H)$^+$; $^1$H NMR (400 MHz, CD$_3$OD): δ 1.08 (br s, 3 H); 1.44 (br s, 3 H); 2.02 (s, 3 H), 2.34 (m, 2 H); 2.54 (m, 2 H); 3.63 (m, 1 H); 3.81 (m, 1 H); 3.97 (m, 1 H); 7.78 (s, 1 H), 7.94 (s, 1 H), Anal. Calcd for C$_{16}$H$_{21}$ClN$_4$O.1.7 TFA: C, 45.23; H, 4.41; N, 10.88. Found: C, 45.51; H, 4.30; N, 11.01.

EXAMPLE 62

6-chloro-2-[(2S)-1-cyclopentyl-2-methylpyrrolidin-2-yl]-1H-benzimidazole-4-carboxamide The title compound as TFA salt was prepared according to the procedure for Example 47, substituting Example 54 for Example 46D and cyclopentanone for formaldehyde. MS (DCI) m/z 347 (M+H)$^+$; $^1$H NMR (400 MHz, CD$_3$OD): δ 1.14 (m, 1 H); 1.59 (m, 3 H); 1.74 (m, 1 H); 1.88 (m, 1 H); 2.03 (s, 3 H); 2.16 (m, 1 H); 2.35 (m, 2 H); 2.50 (m, 2 H); 2.68 (m, 1 H), 3.64 (m, 1 H); 3.80 (m, 1 H); 3.98 (m, 1 H); 7.78 (s, 1 H); 7.92 (s, 1 H). Anal. Calcd for C$_{18}$H$_{23}$ClN$_4$O.1.9 TFA: C, 46.43; H, 4.42; N, 9.94. Found: C, 46.19; H, 4.39; N, 10.33.

EXAMPLE 63

2-[(2S)-1,2-dimethylpyrrolidin-2-yl]-6-fluoro-1H-benzimidazole-4-carboxamide

The title compound as TFA salt was prepared according to the procedure for Example 47, substituting Example 55 for Example 46D. MS (APCI) m/z 277 (M+H)$^+$; $^1$H NMR (400 MHz, CD$_3$OD): δ 1.93 (s, 3 H); 2.35 (m, 2 H); 2.53 (m, 2 H); 2.98 (s, 3 H); 3.55 (m, 1 H); 3.88 (m, 1 H); 7.49 (d, J=8.00 Hz, 1 H) 7.71 (d, J=8.00 Hz, 1 H).

EXAMPLE 64

6-fluoro-2-[(2S)-1-isopropyl-2-methylpyrrolidin-2-yl]-1H-benzimidazole-4-carboxamide The title compound as TFA salt was prepared according to the procedure for Example 47, substituting Example 55 for Example 46D and acetone for formaldehyde. MS (DCI) m/z 305 (M+H)$^+$; $^1$H NMR (400 MHz, CD$_3$OD): δ 1.09 (br s, 3 H); 1.44 (br s, 3 H); 2.01 (s, 3 H); 2.35 (m, 2 H); 2.48 (m, 2 H); 3.62 (m, 1 H); 3.81 (m, 1 H); 3.97 (m, 1 H); 7.51 (dd, J=7.98, 2.45 Hz, 1 H); 7.75 (dd, J=10.43, 2.46 Hz, 1 H).

EXAMPLE 65

2-[(2S)-1-cyclopentyl-2-methylpyrrolidin-2-yl]-6-fluoro-1H-benzimidazole-4-carboxamide The title compound as TFA salt was prepared according to the procedure for Example 47, substituting Example 55 for Example 46D and cyclopentanone for formaldehyde. MS (DCI) m/z 331 (M+H)$^+$; $^1$H NMR(400MHz, CD$_3$OD) δ 1.13 (m, 1 H); 1.60 (m, 3 H); 1.80 (m, 2H); 2.01 (s, 3 H); 2.15 (m, 1 H); 2.33 (m, 2 H); 2.47 (m, 2 H); 2.68 (m, 1 H); 3.62 (m, 1 H); 3.79 (m, 1 H); 3.97 (m, 1 H); 7.51 (dd, J=7.98, 2.45 Hz, 1 H); 7.74 (dd, J=10.43, 2.45 Hz, 1 H).

EXAMPLE 66

2-[(2R)-1,2-dimethylpyrrolidin-2-yl]-6-fluoro-1H-benzimidazole-4-carboxamide

The title compound as TFA salt was prepared according to the procedure for Example 47, substituting Example 56B for Example 46D. MS (DCI) m/z 277 (M+H)$^+$; $^1$H NMR (400 MHz, CD$_3$OD): δ 1.96 (s, 3 H); 2.33 (m, 2 H); 2.53 (m, 2 H); 3.00 (s, 3 H); 3.59 (m, 1 H); 3.90 (m, 1 H); 7.51 (dd, J=7.98, 2.45 Hz, 1 H); 7.74 (dd, J=10.43, 2.45 Hz, 1 H).

EXAMPLE 67

6-fluoro-2-[(2R)-1-isopropyl-2-methylpyrrolidin-2-yl]-1H-benzimidazole-4-carboxamide The title compound as TFA salt was prepared according to the procedure for Example 47, substituting Example 56B for Example 46D and acetone for formaldehyde. MS (DCI) m/z 305 (M+H)$^+$; $^1$H NMR (400 MHz, CD$_3$OD): δ 1.07 (br s, 3 H); 1.43 (br s, 3 H); 2.00 (s, 3 H); 2.35 (m, 2 H); 2.49 (m, 2 H); 3.61 (m, 1 H); 3.79 (m, 1 H); 3.94 (m, 1 H); 7.50 (dd, J=7.98, 2.15 Hz, 1 H); 7.73 (dd, J=10.43, 2.45 Hz, 1 H).

EXAMPLE 68

2-[(2R)-1-cyclopentyl-2-methylpyrrolidin-2-yl]-6-fluoro-1H-benzimidazole4-carboxamide The title compound as TFA salt was prepared according to the procedure for Example 47, substituting Example 56B for Example 46D and cyclopentanone for formaldehyde. MS (DCI) m/z 331 (M+H)$^+$; $^1$H NMR (400 MHz, CD$_3$OD) δ 1.14 (m, 1 H); 1.58 (m,3 H); 1.83 (m,2 H); 2.03 (s, 3 H); 2.15 (m, 1 H); 2.35 (m, 2 H); 2.50 (m, 2 H); 2.70 (m, 1 H); 3.64 (m, 1 H); 3.79 (m, 1 H); 3.98 (m, 1 H); 7.51 (dd, J=7.98, 2.45 Hz, 1 H); 7.73 (dd, J=10.43, 2.45 Hz, 1 H).

EXAMPLE 69

2-[(2R)-1-ethyl-2-methylpyrrolidin-2-yl]-1H-benzimidazole-4-carboxamide

A solution of Example 3B as bis-HCl salt (50 mg, 0.15 mmol) in methanol (3 mL) was treated with triethylamine (63 μL, 0.45 mmol) and acetaldehyde (32 wt % in water, 80 μL, 0.75 mmol) at room temperature for 1 hour. Sodium cyanoborohydride (47 mg, 0.75 mmol) was then added and the solution was stirred at room temperature overnight and at 50° C. for 5 hours. After cooling, the reaction mixture was concentrated and the residue was separated by HPLC (Zorbax, C-18, 250×2.54 column, Mobile phase A: 0.1% TFA in $H_2O$; B: 0.1% TFA in $CH_3CN$; 0-100% gradient) to provide Example 69 as TFA salt. This material was dissolved in 3 niL of 1:1 mixture of methylene chloride and methanol and treated with HCl in ether(1.0 M, 10 mL). Removal of the volatiles afforded Example 69 as HCl salt (57 mg, 96%). MS (APCI/$NH_3$) m/z 273 (M+H)$^+$; $^1$H NMR (400 MHz, $CD_3OD$): δ 1.42 (t, J=6.90 Hz, 3 H), 1.97 (s, 3 H), 2.39 (m, 2 H), 2.55 (m, 2 H), 3.22-3.33 (m, 1 H), 3.55 (m, 2 H), 4.05 (m, 1 H), 7.48 (t, J=7.98 Hz, 1 H), 7.84 (d, J=7.98 Hz, 1 H), 8.03 (d, J=7.67 Hz, 1 H); Anal. Calcd for $C_{15}H_{20}N_4O$.2.9 HCl: C, 47.65; H, 6.10; N, 14.82. Found: C, 47.72; H, 6.58; N, 14.42.

EXAMPLE 70

2-[(2S)-1-ethyl-2-methylpyrrolidin-2-yl]-1H-benzimidazole-4-carboxamide

The title compound as HCl salt was prepared according to the procedure for Example 69, substituting Example 4 for Example 3B. Yield: 85%. MS (DCI/$NH_3$) m/z 273 (M+H)$^+$; $^1$H NMR (400 MHz, $CD_3OD$): δ 1.42 (t, J=6.90 Hz, 3 H), 1.94 (s, 3 H), 2.40 (m, 2 H), 2.53 (m, 2 H), 3.23 (m, 1 H), 3.52 (m, 2 H), 4.06 (m, 1 H), 7.46 (t, J=7.83 Hz, 1 H), 7.82 (d, J=7.98 Hz, 1 H), 8.02 (d, J=7.67 Hz, 1 H); Anal. Calcd for $C_{15}H_{20}N_4O$.2.75 HCl: C, 48.35; H, 6.15; N, 15.04. Found: C, 48.45; H, 6.76; N, 14.58.

EXAMPLE 71

6-chloro-2-(1-ethyl-3-methylpyrrolidin-3-yl)-1H-benzimidazole-4-carboxamide The title compound as HCl salt was prepared according to the procedure for Example 69, substituting Example 46D for Example 3B. Yield: 95%. MS (DCI/$NH_3$) m/z 307 (M+H)$^+$; $^1$H NMR (500 MHz, $CD_3OD$): δ 1.38-1.45 (m, 3 H), 1.82 (s, 3 H), 2.44-2.53 (m, 0.5 H), 2.54-2.62 (m, 0.5 H), 2.86-2.95 (m, 1 H), 3.37-3.54 (m, 3 H), 3.85-4.10 (m, 2.5 H), 4.51 (d, J=12.21 Hz, 0.5 H), 7.91 (d, J=10.37 Hz, 1 H), 8.01 (d, J=8.85 Hz, 1 H); Anal. Calcd for $C_{15}H_{19}ClN_4O$.2.5 HCl: C, 45.27; H, 5.45; N, 14.08. Found: C, 45.45; H, 5.67; N, 13.78.

EXAMPLE 72

2-[(2R)-1,2-dimethylpyrrolidin-2-yl]-1H-benzimidazole-4-carboxamide

The title compound as HCl salt was prepared according to the procedure for Example 47, substituting Example 3B for Example 46D. Yield: 69%. MS (DCI/$NH_3$) m/z 259 (M+H)$^+$; $^1$H NMR (500 MHz, $CD_3OD$): δ 1.97 (s, 3 H), 2.24 (m, 1 H), 2.32-2.41 (m, 2 H), 2.51-2.66 (m, 2 H), 2.99 (s, 3 H), 3.57 (m, 1 H), 3.91 (m, 1 H), 7.47 (t, J=7.78 Hz, 1 H), 7.83 (d, J=7.93 Hz, 1 H), 8.02 (d, J=7.63 Hz, 1 H); Anal. Calcd for $C_{14}H_{18}N_4O$.3 HCl: C, 45.73; H, 5.76; N, 15.24. Found: C, 45.49; H,6.37; N, 14.86.

EXAMPLE 73

2-[(2R)-2-methyl-5-oxopyrrolidin-2-yl]-1H-benzimidazole-4-carboxamide

EXAMPLE 73A

(R)-2-Methyl-5-oxo-pyrrolidine-1,2-dicarboxylic acid-1-tert-butyl ester

To a solution of Example 74D (348 mg, 1.52 mmol) in a mixture of acetonitrile (3 mL), carbon tetrachloride (3 mL) and water (4.6 mL) was added sodium periodate (1.3 g, 6.08 mmol) and ruthenium (III) chloride hydrate (64 mg, 0.30 mmol). This mixture was stirred vigorously at room temperature for 4 days. Solid material was filtered off and the filtrate was partitioned between ethyl acetate and brine. The organic phase was concentrated and the residue was separated by flash chromatography (silica gel, 0-15% gradient methanol in 2:1 EtOAc/hexane) to give the title compound (122 mg, 32%). MS (DCI/$NH_3$) m/z 244 (M+H)$^+$.

EXAMPLE 73B

2-[(2R)-2-methyl-5-oxopyrrolidin-2-yl]-1H-benzimidazole-4-carboxamide

A solution of Example 73A (120 mg, 0.49 mmol) in a mixture of pyridine (3 mL) and DMF (3 mL) was treated with 1,1'-carbonyldiimidazole (88 mg, 0.54 mmol) at 45° C. for 2 h. 2,3-Diamino-benzamide dihydrochloride (110 mg, 0.49 mmol, synthesized as described in previous patent application WO0026192), was added and the mixture was stirred at rt overnight. After concentration under vacuum, the residue was dissolved in acetic acid (6 mL) and heated at 80° C. for 3 hour. After cooled, the reaction mixture was concentrated. The residue was separated by flash chromatography (silica gel, 0-15% gradient MeOH in $CH_2Cl_2$) to give the crude product. This material was further purified by HPLC (Zorbax, C-18, 250×2.54 column, Mobile phase A: 0.1% TFA in $H_2O$; B: 0.1% TFA in $CH_3CN$; 0-100% gradient) to provide Example 73B as TFA salt (80 mg, 36%). MS (DCI/$NH_3$) m/z 259 (M+H)$^+$; $^1$H NMR (400 MHz, $CD_3OD$): δ 1.88 (s, 3 H), 2.41-2.48 (m, 1 H), 2.50-2.55 (m, 2 H), 2.58-2.66 (m, 1 H), 7.48(t, J=7.67 Hz, 1 H), 7.81 (d, J=7.98 Hz, 1 H), 7.97 (d, J=7.67 Hz, 1 H); Anal. Calcd for $C_{13}H_{14}N_4O_2$.1.75 TFA: C, 43.29; H, 3.47; N, 12.24. Found: C, 43.29; H,3.85; N, 12.38.

EXAMPLE 74

(R)-2-methyl-pyrrolidine-1,2-dicarboxylic acid 1-tert-butyl ester

EXAMPLE 74A

L-Alanine benzyl ester hydrochloride (24.0 g), acetonitrile (96 mL), 1-bromo-3-chloropropane (70.6 g) and N,N-diisopropylethylamine (43.2 g) were charged to a reactor. The reaction mixture was warmed to 30° C. for 74 hours. The reaction mixture was cooled to 20° C. and quenched with 2N citric acid (112 g). The aqueous phase was extracted twice with heptane (72 g each). The pH of the aqueous phase was adjusted to pH 5.8-6.0 with 4N NaOH solution. The product was extracted from the aqueous phase with methyl tert-butyl ether (twice with 122 mL then once with 100 mL). The combined organic phases were washed with saturated sodium bicarbonate solution (76 mL) and 25% brine (48 mL). The organic phase was dried by passing it through a bed of sodium sulfate and distilling it to approximately half of the original volume, and was used without further purification (assay yield was 20.9 g, 73%).

EXAMPLE 74B

Example 74A (10.2 g, as solution in 81 mL methyl tert-butyl ether) was charged to a reactor containing di-tert-butyl-dicarbonate (10.0 g). This mixture was stirred at 25° C. overnight N,N-dimethylethylenediamine (1.15 g) was then charged to react with the excess di-tert-butyldicarbonate.

After mixing at 25° C. overnight a sample was taken for NMR analysis. The reaction mixture was then washed twice with 1N H$_3$PO$_4$ solution (27 g each), then with 5% NaHCO$_3$ (28 g), water (27 g), and brine (36 g). The product solution was dried with Na$_2$SO$_4$, and then concentrated. Following a chase distillation with toluene the product solution for 13.9 g (96% yield). The solution was used without further purification.

EXAMPLE 74C

Example 74B (60 wt % solution in toluene, 50.0 g, 30.0 g assay) was diluted with DMF (240 mL) was added and the solution was cooled to <−20° C. Lithium bis(trimethylsilyl) amide (25 wt % in THF, 70 g) was added continuously over ~3 hours, such that the internal temperature was maintained. The reaction was quenched into 10 wt % aq. NH$_4$Cl (250 g). The resulting mixture was extracted twice with heptane (225 mL each). The combined heptane layers were washed with 10% NaCl solution (206 g) then 20% NaCl solution (201 g). The heptane layer was distilled, then isopropyl acetate was added (175 mL) and distilled. More isopropyl acetate (175 mL) was added and the solution was filtered, then more isopropyl acetate (0.7 kg /kg SM) was used as a rinse. Finally, the isopropyl acetate was distilled to ~40 g, and used without further purification for an assay of 27.4 g (102%). $^1$H NMR (400 MHz, CDCl$_3$), as a ~2:1 mixture of rotamers δ ppm 1.35 (s, 6 H) 1.41 (s, 3 H) 1.54 (s, 2 H) 1.60 (s, 1 H) 1.77-1.97 (m, 3 H) 2.08-2.22 (m, 1 H) 3.39-3.64 (m, 2 H) 5.02-5.24 (m, 2 H) 7.26-7.38 (m,5 H)

EXAMPLE 74D (R)-2-methyl-pyrrolidine-1,2-dicarboxylic acid 1-tert-butyl ester A pressure reactor was charged with 5% palladium on carbon (2.56 g) and purged with nitrogen. Example 74C (~60 wt % solution in isopropyl acetate, 83.1 g assay) was added, along with denatured EtOH (335 g). The reactor was pressurized with hydrogen (40 psig). The hydrogenolysis was continued while maintaining a reaction temperature under 40° C. The catalyst was filtered off to afford 97% assay yield, 93.9% ee product. The solvents were distilled under vacuum and chased with isopropyl acetate (240 g). The resulting solution was further chased with heptanes (200 g), then additional heptanes (500 g) were added and heated to reflux until all solids dissolved. After cooling to 20° C., the solids were collected by filtration and washed with heptane (80 g) and dried to yield 54.8 g (88% yield) of Example 74D. $^1$H NMR (400 MHz, CDCl$_3$, mixture of rotamers) δ ppm 1.42 (s) and 1.47 (s), (9 H); 1.52 (s) and 1.61 (s) (2 H); 1.73-2.05 (m, 3 H) 2.19-2.38 (m) and 2.46-2.67 (m) (1H); 3.26-3.71 (m, 2 H).

What is claimed is:

1. A compound of Formula (I)

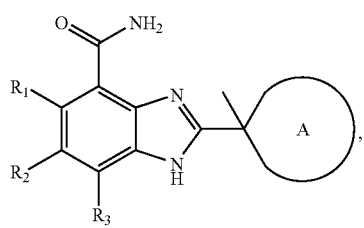

(I)

or a therapeutically acceptable salt thereof, wherein

R$_1$, R$_2$, and R$_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, NR$_A$R$_B$, and (NR$_A$R$_B$)carbonyl;

A is a nonaromatic 4, 5, 6, 7, or 8-membered ring that contains 1 or 2 nitrogen atoms and, optionally, one sulfur or oxygen atom, wherein the nonaromatic ring is optionally substituted with 1, 2, or 3 substituents selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, nitro, NR$_C$R$_D$, (NR$_C$R$_D$)alkyl, (NR$_C$R$_D$)carbonyl, (NR$_C$R$_D$)carbonylalkyl, (NR$_C$R$_D$)sulfonyl, and oxo; and R$_A$, R$_B$, R$_C$, and R$_D$ are independently selected from the group consisting of hydrogen, alkyl, and alkycarbonyl.

2. The compound according to claim 1 wherein

R$_1$, R$_2$, and R$_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, NR$_A$R$_B$, and (NR$_A$R$_B$)carbonyl;

A is selected from the group consisting of

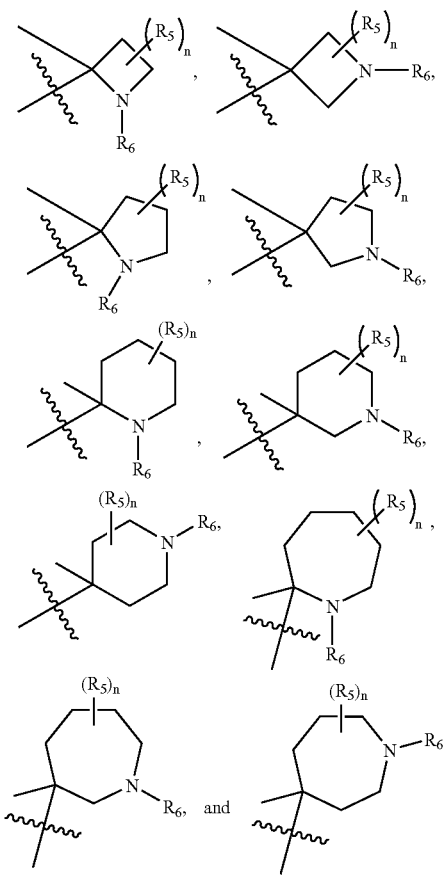

R$_5$ is independently selected from the group consisting of alkenyl, alkoxy, alkoxycarbonyl, alkyl, alkynyl, haloalkoxy, haloalkyl, halogen, hydroxy, hydroxyalkyl, $NR_CR_D$, and $(NR_CR_D)$carbonyl;

n is 0, 1, 2, or 3;

$R_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, $(NR_CR_D)$alkyl, $(NR_CR_D)$carbonyl, $(NR_CR_D)$carbonylalkyl, and $(NR_CR_D)$sulfonyl;

$R_A$ and $R_B$ are independently selected from the group consisting of hydrogen, alkyl, and alkycarbonyl; and $R_C$ and $R_D$ are independently selected from the group consisting of hydrogen and alkyl.

3. The compound according to claim 2 wherein A is selected from the group consisting of

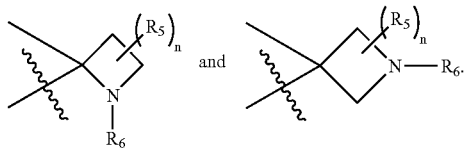

4. The compound according to claim 3 wherein $R_1$, $R_2$, $R_3$, and $R_5$ are hydrogen;

n is 0;

$R_6$ is selected from the group consisting of hydrogen, alkyl, arylalkyl, cycloalkyl, cycloalkylalkyl, heterocycle, heteroarylalkyl, and $(NR_CR_D)$sulfonyl; and $R_C$ and $R_D$ are independently selected from the group consisting of hydrogen and alkyl.

5. The compound according to claim 2 wherein A is selected from the group consisting of

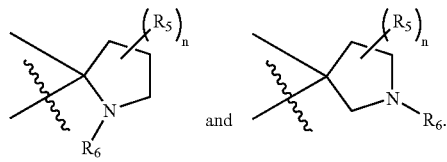

6. The compound according to claim 5 wherein $R_1$, $R_2$, $R_3$, and $R_5$ are hydrogen;

n is 0;

$R_6$ is selected from the group consisting of hydrogen, alkyl, arylalkyl, cycloalkyl, cycloalkylalkyl, heterocycle, heteroarylalkyl, and $(NR_CR_D)$sulfonyl; and $R_C$ and $R_D$ are independently selected from the group consisting of hydrogen and alkyl.

7. The compound according to claim 2 wherein A is selected from the group consisting of

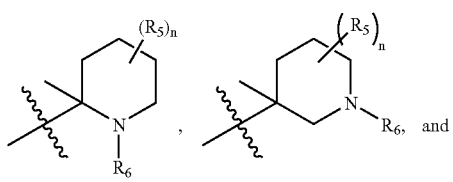

-continued

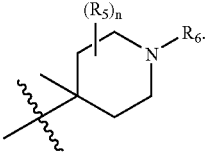

8. The compound according to claim 7 wherein $R_1$, $R_2$, $R_3$, and $R_5$ are hydrogen;

n is 0;

$R_6$ is selected from the group consisting of hydrogen, alkyl, arylalkyl, cycloalkyl, cycloalkylalkyl, heterocycle, heteroarylalkyl, and $(NR_CR_D)$sulfonyl; and $R_C$ and $R_D$ are independently selected from the group consisting of hydrogen and alkyl.

9. The compound according to claim 2 wherein A is selected from the group consisting of

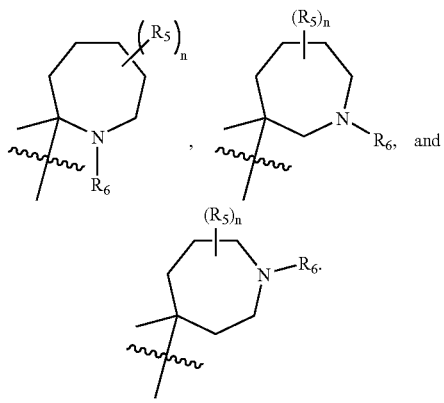

10. The compound according to claim 9 wherein $R_1$, $R_2$, $R_3$, and $R_5$ are hydrogen;

n is 0;

$R_6$ is selected from the group consisting of hydrogen, alkyl, arylalkyl, cycloalkyl, cycloalkylalkyl, heterocycle, heteroarylalkyl, and $(NR_CR_D)$sulfonyl; and $R_C$ and $R_D$ are independently selected from the group consisting of hydrogen and alkyl.

11. A compound selected from the group consisting of 2-(2-methylpyrrolidin-2-yl)-1H-benzimidazole-4-carboxamide;

2-[(2R)-2-methylpyrrolidin-2-yl]-1H-benzimidazole-4-carboxamide;

2-[(2S)-2-methylpyrrolidin-2-yl]-1H-benzimidazole-4-carboxamide;

2-(1,2-dimethylpyrrolidin-2-yl)-1H-benzimidazole-4-carboxamide;

2-(1-ethyl-2-methylpyrrolidin-2-yl)-1H-benzimidazole-4-carboxamide;

2-(2-methyl-1-propylpyrrolidin-2-yl)-1H-benzimidazole-4-carboxamide;

2-(1-isopropyl-2-methylpyrrolidin-2-yl)-1H-benzimidazole-4-carboxamide;

2-(1-cyclobutyl-2-methylpyrrolidin-2-yl)-1H-benzimidazole-4-carboxamide;

2-(3-methylpyrrolidin-3-yl)-1H-benzimidazole-4-carboxamide;

2-(3-methyl-1-propylpyrrolidin-3-yl)-1H-benzimidazole-4-carboxamide;

2-[1-(cyclopropylmethyl)-3-methylpyrrolidin-3-yl]-1H-benzimidazole-4-carboxamide;
2-(1-isobutyl-3-methylpyrrolidin-3-yl)-1H-benzimidazole-4-carboxamide;
2-(1-isopropyl-3-methylpyrrolidin-3-yl)-1H-benzimidazole-4-carboxamide;
2-(1-cyclobutyl-3-methylpyrrolidin-3-yl)-1H-benzimidazole-4-carboxamide;
2-(1-cyclopentyl-3-methylpyrrolidin-3-yl)-1H-benzimidazole-4-carboxamide;
2-(1-cyclohexyl-3-methylpyrrolidin-3-yl)-1H-benzimidazole-4-carboxamide;
2-(3-methyl-1-tetrahydro-2H-pyran-4-ylpyrrolidin-3-yl)-1H-benzimidazole-4-carboxamide;
2-[3-methyl-1-(pyridin4-ylmethyl)pyrrolidin-3-yl]-1H-benzimidazole-4-carboxamide;
2-[3-methyl-1-(2-phenylethyl)pyrrolidin-3-yl]-1H-benzimidazole-4-carboxamide;
2-[3-methyl-1-(1-methyl-3-phenylpropyl)pyrrolidin-3-yl]-1H-benzimidazole-4-carboxamide;
2-(2-methylazetidin-2-yl)-1H-benzimidazole-4-carboxamide;
2-(1-isopropyl-2-methylazetidin-2-yl)-1H-benzimidazole-4-carboxamide;
2-(1-cyclobutyl-2-methylazetidin-2-yl)-1H-benzimidazole-4-carboxamide;
2-(1-cyclopentyl-2-methylazetidin-2-yl)-1H-benzimidazole-4-carboxamide;
2-(1-cyclohexyl-2-methylazetidin-2-yl)-1H-benzimidazole-4-carboxamide;
2-(3-methylazetidin-3-yl)-1H-benzimidazole-4-carboxamide;
2-(3-methyl-1-propylazetidin-3-yl)-1H-benzimidazole-4-carboxamide;
2-[1-(cyclopropylmethyl)-3-methylazetidin-3-yl]-1H-benzimidazole-4-carboxamide;
2-(1-isobutyl-3-methylazetidin-3-yl)-1H-benzimidazole-4-carboxamide;
2-(1-cyclobutyl-3-methylazetidin-3-yl)-1H-benzimidazole-4-carboxamide;
2-(1-cyclopentyl-3-methylazetidin-3-yl)-1H-benzimidazole-4-carboxamide;
2-(1-cyclohexyl-3-methylazetidin-3-yl)-1H-benzimidazole-4-carboxamide;
2-(3-methyl-1-tetrahydro-2H-pyran-4-ylazetidin-3-yl)-1H-benzimidazole-4-carboxamide;
2-{1-[(dimethylamino)sulfonyl]-3-methylazetidin-3-yl}-1H-benzimidazole-4-carboxamide;
2-(2-methylpiperidin-2-yl)-1H-benzimidazole-4-carboxamide;
2-(2-methyl-1-propylpiperidin-2-yl)-1H-benzimidazole-4-carboxamide;
2-{1-[(dimethylamino)sulfonyl]-4-methylpiperidin-4-yl}-1H-benzimidazole-4-carboxamide;
2-(1-cyclobutyl-4-methylpiperidin-4-yl)-1H-benzimidazole-4-carboxamide;
2-(1-isopropyl-4-methylpiperidin-4-yl)-1H-benzimidazole-4-carboxamide;
2-(4-methyl-1-propylpiperidin-4-yl)-1H-benzimidazole-4-carboxamide;
2-(4-methylazepan-4-yl)-1H-benzimidazole-4-carboxamide;
2-(1-cyclopentyl-4-methylazepan-4-yl)-1H-benzimidazole-4-carboxamide; and
2-(1-Cyclohexyl-4-methyl-azepane-4-yl)-H-benzoimidazole-4-carboxylic acid amide.

12. A compound selected from the group consisting of
2-[1-(2-fluorobenzyl)-3-methylpyrrolidin-3-yl]-1H-benzimidazole-4-carboxamide;
6-chloro-2-(3-methylpyrrolidin-3-yl)-1H-benzimidazole-4-carboxamide;
6-chloro-2-(1,3-dimethylpyrrolidin-3-yl)-1H-benzimidazole-4-carboxamide;
6-chloro-2-(1-isopropyl-3-methylpyrrolidin-3-yl)-1H-benzimidazole-4-carboxamide;
2-(2-methylpyrrolidin-2-yl)-6-(trifluoromethyl)-1H-benzimidazole-4-carboxamide;
2-(1,2-dimethylpyrrolidin-2-yl)-6-(trifluoromethyl)-1H-benzimidazole-4-carboxamide;
6-fluoro-2-(2-methylpyrrolidin-2-yl)-1H-benzimidazole-4-carboxamide;
6-fluoro-2-(2-methylpyrrolidin-2-yl)-1H-benzimidazole-4-carboxamide;
6-chloro-2-(2-methylpyrrolidin-2-yl)-1H-benzimidazole-4-carboxamide;
6-chloro-2-[(2R)-2-methylpyrrolidin-2-yl]-1H-benzimidazole-4-carboxamide;
6-chloro-2-[(2S)-2-methylpyrrolidin-2-yl]-1H-benzimidazole-4-carboxamide;
6-fluoro-2-[(2S)-2-methylpyrrolidin-2-yl]-1H-benzimidazole-4-carboxamide;
6-fluoro-2-[(2R)-2-methylpyrrolidin-2-yl]-1H-benzimidazole-4-carboxamide;
6-chloro-2-[(2R)-1,2-dimethylpyrrolidin-2-yl]-1H-benzimidazole-4-carboxamide;
6-chloro-2-[(2R)-1-isopropyl-2-methylpyrrolidin-2-yl]-1H-benzimidazole-4-carboxamide;
6-chloro-2-[(2R)-1-cyclopentyl-2-methylpyrrolidin-2-yl]-1H-benzimidazole-4-carboxamide;
6-chloro-2-[(2S)-1,2-dimethylpyrrolidin-2-yl]-1H-benzimidazole-4-carboxamide;
6-chloro-2-[(2S)-1-isopropyl-2-methylpyrrolidin-2-yl]-1H-benzimidazole-4-carboxamide;
6-chloro-2-[(2S)-1-cyclopentyl-2-methylpyrrolidin-2-yl]-1H-benzimidazole-4-carboxamide;
2-[(2S)-1,2-dimethylpyrrolidin-2-yl]-6-fluoro-1H-benzimidazole-4-carboxamide;
6-fluoro-2-[(2S)-1-isopropyl-2-methylpyrrolidin-2-yl]-1H-benzimidazole-4-carboxamide;
2-[(2S)-1-cyclopentyl-2-methylpyrrolidin-2-yl]-6-fluoro-1H-benzimidazole-4-carboxamide;
2-[(2R)-1,2-dimethylpyrrolidin-2-yl]-6-fluoro-1H-benzimidazole-4-carboxamide;
6-fluoro-2-[(2R)-1-isopropyl-2-methylpyrrolidin-2-yl]-1H-benzimidazole-4-carboxamide;
2-[(2R)-1-cyclopentyl-2-methylpyrrolidin-2-yl]-6-fluoro-1H-benzimidazole-4-carboxamide;
2-[(2R)-1-ethyl-2-methylpyrrolidin-2-yl]-1H-benzimidazole-4-carboxamide;
2-[(2S)-1-ethyl-2-methylpyrrolidin-2-yl]-1H-benzimidazole-4-carboxamide;
6-chloro-2-(1-ethyl-3-methylpyrrolidin-3-yl)-1H-benzimidazole-4-carboxamide;
2-[(2R)-1,2-dimethylpyrrolidin-2-yl]-1H-benzimidazole-4-carboxamide; and
2-[(2R)-2-methyl-5-oxopyrrolidin-2-yl]-1H-benzimidazole-4-carboxamide.

13. 2-(2-methylpyrrolidin-2-yl)-1H-benzimidazole-4-carboxamide or a therapeutically acceptable salt thereof.

14. The compound of claim 13, wherein the compound is 2-((R)-2-methylpyrrolidin-2-yl)-1H-benzimidazole-4-carboxamide, or a therapeutically acceptable salt thereof.

15. The compound of claim 13, wherein the compound is 2-[(2S)-2-methylpyrrolidin-2-yl]-1H-benzimidazole-4-carboxamide, or a therapeutically acceptable salt thereof.

16. The compound of claim 14, wherein the therapeutically acceptable salt is hydrochloride.

17. A pharmaceutical composition comprising is 2-((R)-2-methylpyrrolidin-2-yl)-1H-benzimidazole-4-carboxamide in combination with a therapeutically acceptable carrier.

* * * * *

UNITED STATES PATENT AND TRADEMARK OFFICE
CERTIFICATE OF CORRECTION

PATENT NO. : 7,550,603 B2
APPLICATION NO. : 11/401638
DATED : June 23, 2009
INVENTOR(S) : Zhu et al.

It is certified that error appears in the above-identified patent and that said Letters Patent is hereby corrected as shown below:

Column 59, line 15, claim 11: "pyridin4-ylmethyl" to read as --pyridin-4-ylmethyl--

Column 59, line 65, claim 11: "Cyclohexyl" to read as --cyclohexyl--

Column 62, line 01, claim 17: "comprising is" to read as --comprising--

Signed and Sealed this
Thirteenth Day of March, 2012

David J. Kappos
*Director of the United States Patent and Trademark Office*